United States Patent [19]

Kaneyasu et al.

[11] Patent Number: 4,638,443
[45] Date of Patent: Jan. 20, 1987

[54] GAS DETECTING APPARATUS

[75] Inventors: Masayoshi Kaneyasu; Hideo Arima, both of Yokohama; Mitsuko Ito, Yokosuka; Shoichi Iwanaga, Yokohama; Nobuo Sato, Yokosuka; Takanobu Noro; Akira Ikagami, both of Yokohama; Tokio Isogai, Hitachi, all of Japan

[73] Assignee: Hitachi, Ltd., Tokyo, Japan

[21] Appl. No.: 581,667

[22] Filed: Feb. 21, 1984

[30] Foreign Application Priority Data

Feb. 21, 1983 [JP] Japan ................................. 58-26166

[51] Int. Cl.$^4$ ................. G01N 27/12; G06F 15/20; G08B 17/10
[52] U.S. Cl. ........................................ 364/497; 73/23; 340/634
[58] Field of Search ............... 340/632, 633, 634; 364/496, 497, 498; 73/23, 27 R

[56] References Cited

U.S. PATENT DOCUMENTS

| 4,390,869 | 6/1983 | Christen et al. | 340/634 X |
| 4,443,791 | 4/1984 | Risgin et al. | 340/634 |
| 4,457,161 | 7/1984 | Iwanaga et al. | 73/23 |
| 4,458,242 | 7/1984 | Kusanagi et al. | 340/634 |
| 4,490,715 | 12/1984 | Kusanagi et al. | 340/634 |
| 4,542,640 | 9/1985 | Clifford | 73/23 |

OTHER PUBLICATIONS

Kim Ki-Wan et al., Fabrication of Semiconductor Gas Sensors and Their Electrical Characteristics, J. Korea Inst. Electron Engineering, vol. 15, No. 5, Oct. 1978.

Primary Examiner—Felix D. Gruber
Attorney, Agent, or Firm—Antonelli, Terry & Wands

[57] ABSTRACT

A gas detecting apparatus incorporates a number of gas detecting elements which react with a variety of gases and exhibit gas sensitivities differing from one another in dependence on the gas species. The detection patterns obtained by quantitizing the detection outputs of the gas detecting elements are compared with a plurality of standard patterns prepared previously for assumed combinations of gas species and concentrations thereof. On the basis of the standard pattern which is same or most similar to the detection pattern, the gas species is identified.

7 Claims, 34 Drawing Figures

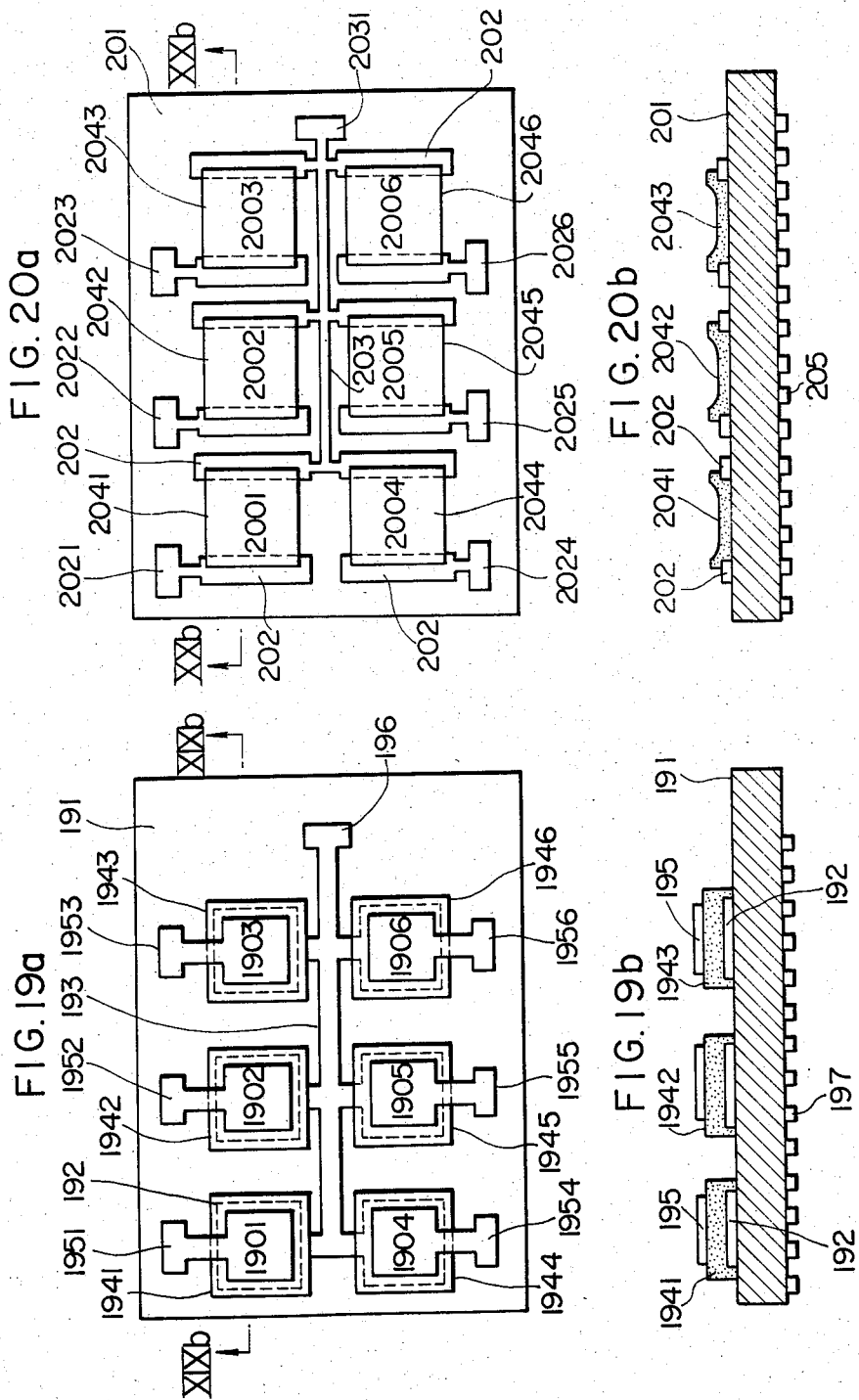

GAS DETECTING APPARATUS

BACKGROUND OF THE INVENTION

1. Field of the Invention

The present invention generally relates to a gas detecting apparatus and more particularly to a gas detecting apparatus for detecting gas information such as the sort or species of a particular, gas and concentration thereof or the species of a gas or gases mixed with a known gas at a given or specific ratio as well as concentration of the gas.

2. Description of the Prior Art

Heretofore, semiconductor gas detecting elements made of tin oxide ($SnO_2$), iron oxide ($Fe_2O_3$), zinc oxide (ZnO) or the like which have such a characteristic that the electric conductivity changes in dependence on gas concentration have been widely employed in the gas detecting apparatus because of ease of handling and inexpensiveness. Operation of such semiconductor gas detecting element is based on the principle that when a reducible gas of an electron releasing nature such as hydrogen and hydrocarbon is absorbed on an active surface of an n-type semiconductor such as $SnO_2$ and ZnO, conductivity of the semiconductor is increased due to an increase in the density of electrons. On the other hand, the conductivity is decreased upon absorption of a gas of an electron pulling nature such as oxygen gas because of decrease in the electron density. On the other hand, in the case of a p-type semiconductor element use is made of the phenomenon that conductivity if decresed upon absorption of the gas of an electron releasing type while absorption of an electron pulling gas involves increasing in the conductivity in reverse to the case of the n-type semiconductor element.

FIG. 1 shows graphically a typical detection characteristic curve 12 representing detection of propane ($C_3H_8$) gas by a $SnO_2$-detector or sensor element. As will be seen from this figure, the $SnO_2$-sensor element can be satisfactorily employed for practical measurements because the conductivity of the element varies as a definite function of concentration of the detected gas. Unfortunately, however, the gas sensor element used almost universely seldom exhibits a selective sensitivity only to a particular sort of gas. Instead, it typically responds with different detection characteristics to various gases such as methane ($CH_4$), hydrogen ($H_2$) and ethanol vapor ($C_2H_5OH_g$), respectively, as indicated by curves 11, 13 and 14 in FIG. 1. Besides, the detection output signal produced in response to the presence of combustible gases such as methane, propane and the like is at a lower level than the detection signal produced in response to the presence of organic solvent vapor typified by an ethanol vapor for a given concentration, as will be seen from FIG. 1. Under these circumstances, attempts to realize the selective detection of a specific gas, inter alia the combustible gas, by using the conventional semiconductor gas sensor element have encounted great technical difficulty in dealing with the detection outputs produced in response to the other gases than the desired one.

As an approach to solve the problem mentioned above, there have been proposed a method and an apparatus in which a plurality of gas sensor elements having respective gas detection characteristics differing from one another are used for realizing qualitative and quantitative identifications of a corresponding number of different gases. By way of example, Japanese Patent Application Laid-Open No. 80192/1975 discloses a gas detecting method according to which a sensor element Sab capable of detecting a gas a and another gas b is provided in combination with a sensor element Sb capable of selectively detecting only the gas b for detecting the gas a in case the element capable of detecting selectively only the gas a is unavailable. With this method, the presence or absence of the gas a can be discriminably determined by ascertaining that the element Sb detects the gas b simultaneously with detection of a certain gas by the sensor element Sab. Some inventors of the present application have also proposed a mixed gas detecting apparatus which includes a plurality of gas detecting elements of which gas detection characteristics are previously measured for allowing measurement of the gas information such as species and concentrations of gas components of a gas mixture containing gas components known per se. Reference may be made to U.S. patent application Ser. No. 336,304 filed Dec. 31, 1981, and now abandoned.

However, the method and the apparatus mentioned above as well as those similar to them suffer difficulties mentioned below. Namely, the first mentioned method is considerably limited in respect to the possible combinations of two types of gases which can be measured. This is because the element capable of selectively detecting only one of the gases can not be realized unless the mechanism of gas detection of the gas sensor elements is differentiated for two types of combined gases. Second, the quantitative identification of the gas concentration can not be realized with a signal processing circuit of a simple configuration. This is particularly true in the case where two types of gases simultaneously come into contact with the sensor elements.

The last mentioned proposal has certainly reduced the drawbacks of the former to a significant degree and broadened the range of applications. However, since the number of gas information is inherently less than the number of the incorporated sensors, an increased number of the sensor elements are necessarily required to be provided in order to render more gas information to be available. In this connection, it should be mentioned that the last mentioned system is operative on the basis of characteristic functions which approximate the gas detection characteristics of the individual elements as measured previously, wherein predetermined gas information is derived by processing the gas detection outputs of the individual sensor elements through algebraical procedures. As the consequence, the increased number of the sensor elements will involve surprisingly increased expenditure for executing the algebraical procedures to derive the aimed gas information, which in turn results in a significantly enlarged scale of the signal processing circuit. For example, when a microprocessor is used for the signal processing, storage means of an enormous capacity will be required. Further, accuracy of the arithmetic operation will be degraded due to accumulation of errors occurring in the course of processing. For these reasons, the performances of the gas sensor elements themselves are required to be highly sophisticated in order to dispose of the problems involved by increasing the number of the incorporated sensor elements, although the last mentioned approach may work adequately from the theoritical viewpoint. In this way, there exists a limitation in the number of the sensor elements which can be used in the last mentioned system.

SUMMARY OF THE INVENTION

An object of the present invention is to provide gas detecting apparatus of small size and low manufacturing cost which is capable of detecting at a high speed and with an improved accuracy the gas information such as species and concentrations of individual gases and gas mixtures or gas components thereof in a number far exceeding that of sensor elements, which may thus be incorporated in the apparatus in a requisite minimum number.

In view of the above object, the gas detecting apparatus according to the present invention includes an appropriate number of gas sensor elements which react with a great variety of gases and exhibit gas sensitivities differing from one another in dependence on the species of gases. Detection patterns in a histogram derived by quantitizing the detection outputs of these gas sensor elements are compared with a plurality of standard patterns previously prepared for assumed combinations of species and concentrations of component gases and stored in storage means, so that the species of the component gases can be identified on the basis of the same or most similar standard pattern. According to the teachings of the invention, a number of various gases which exceed the number of the incorporated sensor elements can be qualitatively identified. In succession to the qualitative identification, concentration of the identified gas can be determined with an improved accuracy on the basis of the output signal produced by the sensor element which exhibits the highest sensitivity to the identified gas.

BRIEF DESCRIPTION OF THE DRAWINGS

FIGS. 3a to 3c show schematically a structure of a three-element integrated sensor unit according to an embodiment of the invention, wherein FIG. 3a is a top plan view of the same, FIG. 3b is a bottom plan view and FIG. 3c is a sectional view taken along the line A—A' in FIG. 3a.

FIGS. 19a and 19b are views schematically showing a structure of a six-element integrated sensor unit, wherein FIG. 19a is a plan view of the same and FIG. 19b is a sectional view taken along the line A—A' in FIG. 19a.

FIGS. 20a and 20b are views showing another example of the six-element integrated sensor unit, wherein FIG. 20a is a plan view and FIG. 20b is a sectional view taken along the line A—A' in FIG. 20a.

DESCRIPTION OF THE PREFERRED EMBODIMENTS

Before entering into description of the exemplary embodiment of the invention, the underlying principle will first be elucidated briefly, defining that the electric conductivity where a specified gas is not present is $G_0$ and the conductivity where the gas comes in is G.

Figure 1:
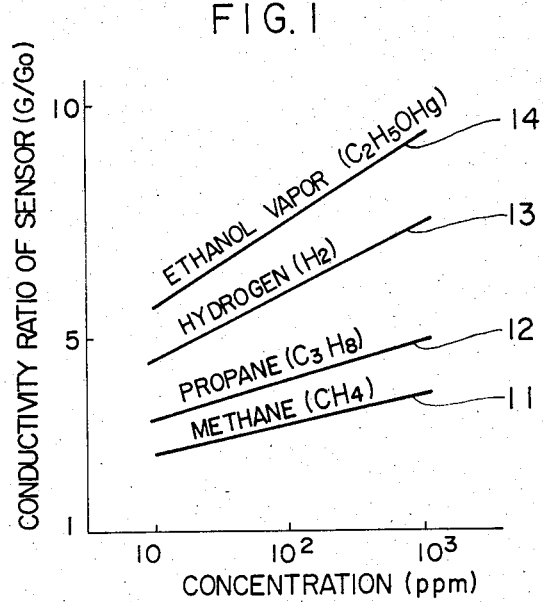
FIGS. 1 and 2 are views showing actually maasured detection characteristics of semiconductor gas sensor elements.
Figure 2:
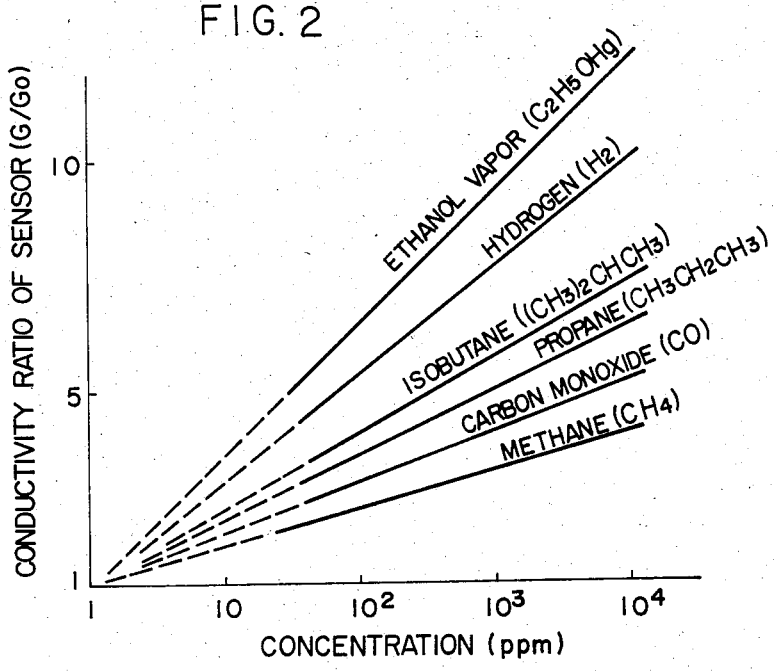

The gas detection characteristic of a gas detector or sensor element made of tin oxide ($SnO_2$) is in general such as shown in FIG. 2 in which ratio of conductivity $G/G_0$ of the sensor element is taken along the ordinate in a logarithmic scale while gas concentration C (ppm) is taken along the abscissa in logarithmic scale. It will be seen from FIG. 2 that the conductivity ratio $G/G_0$ varies linearly as a function of the gas concentration C (ppm), and that the linear variation has a slope which is discriminably different in dependence on the sort or variety of gas. Further, magnitude of the slope represents the sensitivity of the sensor element to the corresponding variety of gas. The gas detection characteristic illustrated in FIG. 2 may be expressed in a mathematical form such as follows:

$$G/G_0 = b(C+l)^m \tag{1}$$

where m is a characteristic value representing the gas sensitivity of the sensor element, and b and l are correcting values for adjusting the origin of the logarithmic coordinate system. For satisfying the boundary conditions given by $$G/G_0 = 1 \text{ and } C=0 \tag{2}$$

must be as follows:

$$b = l^{-m} \tag{3}$$

With the expression (3) being taking into consideration, the expression (1) may be rewritten as follows:

$$G/G_0 = (\alpha C + 1)^m \tag{4}$$

where a represents a correcting coefficient or factor for adjusting the origin of the coordinate system and may take different numerical values in dependence on the types of gas independent of the material or composition of the sensor element, while the characteristic value m may differ in dependence on both the sort of the sensor material and that of gas.

The characteristics mentioned above are generally observed in the metal oxide semiconductor gas sensing elements typified by the $SnO_2$ gas sensor element. Under the circumstance, realization of the sensor elements having mutually different values of m may be readily accomplished by correspondingly changing the composition or material of the sensor element, e.g. by replacing $SnO_2$ with zinc oxide (ZnO), tungsten oxide ($WO_3$) or the like, by adding catalyst such as platinum (Pt) or palladium (Pd) to the material of the sensor element or changing the amount of catalyst to be added, or by modifying the process or conditions for manufacturing the sensor element.

The principle underlying the present invention will be elucidated on the assumption that a gas detecting apparatus or system which includes N gas detecting elements (or sensor elements) having gas detecting characteristics (i.e. values of m) which differ from one another is used for identifying disciminably M sorts of gases, by way of example.

The technological concept underlying the present invention is based on the established fact that patterns depicted or traced by the detection signals outputted from the sensor elements upon detection of gases differ from one another in dependence on the sorts of gases and concentrations thereof and resides in that the patterns thus obtained are analyzed through a pattern recognition processing to thereby make available the gas information of the sort or type and concentration of the gas which comes to contact with the sensor elements. More particularly, from the expression (4), the detection output $(G/G_0)_j$ produced by a sensor element j upon detection of a gas i of concentration C (ppm) is represented by $$(G/G_0)_j = (\alpha_i C + 1)^{m_{ij}} \quad (5)$$

where $i = 1, 2, \ldots$ or M and $j = 1, 2, \ldots$ or N. In the above expression (5), $\alpha_i$ represents a correcting factor for the gas i to be detected and $m_{ij}$ represents the characteristic value of the detector or sensor elexent for the gas i to be detected. When both sides of the expression (5) are logarithmically rewritten and processed in the manner defined by expressions (6) et seq., a numerical value $p_j^i$ which is independent of the concentration C can be obtained as given by expression (7).

$$\frac{\log (G/G_0)_j}{\sum_{j=1}^{N} \log (G/G_0)} = \frac{\log (\alpha_i C + 1)^{m_{ij}}}{\sum_{j=1}^{N} \log (\alpha_i C + 1)^{m_{ij}}} \quad (6)$$

$$= \frac{m_{ij} \cdot \log (\alpha_i C + 1)}{\log (\alpha_i C + 1) \cdot \sum_{j=1}^{N} m_{ij}}$$

$$= \frac{m_{ij}}{\sum_{j=1}^{N} m_{ij}} \quad (= p_j^i) \quad (7)$$

From the expression (7), it is obvious that the numerical value $p_j^i$ satisfies the condition given by the following expression:

$$\sum_{j=1}^{N} p_j^i = 1 \quad (8)$$

It will be seen that the mathematical procedure mentioned above is nothing but a standardizing procedure of numerical values according to a general method of numerical data processing, and that vector $p^i$ having the value $p_j^i$ thus obtained as the j-th component may be regarded and referred to as a standard pattern depicted by the output signals produced by N sensor elements upon detection of the gas i. Thus, the number of the patterns which can be utilized as the standard patterns, that is, the number of the gas species which can be discriminably detected is independent of the number of the detector or sensor elements incorporated in the gas detecting apparatus in concern. Accordingly, any number of gas species can be identified so far as the standard patterns of the gases to be detected are different from one another.

By comparing the pattern depicted by the output signals of N sensor elements produced upon detection of a gas with each of the standard patterns thus prepared, it is possible to identify the gas corresponding to the standard pattern which is most similar to the detected pattern as the gas which comes to contact with the sensor elements. In the identification mentioned above, the concept of distance in Euclidean space of N dimensions is introduced. More particularly, distance $d^i$ between two patterns is calculated in accordance with the following expression:

$$d^i = (\| \vec{x} - \vec{p}^i \|_2)^2 \quad (9)$$

$$= \sum_{j=1}^{N} (x_j - p_j^i)^2$$

where $\vec{x}$ represents the N-dimensional vector expressing the detected pattern and $x_j$ represents the j-th component of the vector $\vec{x}$ which satisfies the following condition:

$$\sum_{j=1}^{N} x_j = 1 \quad (10)$$

When i is determined which satisfies d min given by $$d \min = \min_i \{d^i\} \quad (11)$$

the sort or kind of the gas (species of gas) which comes to contact with the sensor elements can be identified.

When the standard pattern $\vec{p}^i$ which is independent of the concentration as given by the expression (7) is not available, i.e. when such sort of gas is present for which the detection pattern undergoes changes in dependence on variation in the concentration, either of the below mentioned measures may be taken.

(1) In case the detection pattern is similar to one standard pattern in spite of variation of some degree and is obviously distinct from the other standard patterns:

Assuming that this sort of gas is represented by a suffix i, a set of detection patterns $\{p_k^i\}$ where $k = 1, 2, .$ .. or $L^i$ determined for $L^i$ different concentrations of the gas i, respectively, are handled as one class through the procedure described hereinafter for calculating the distance $d^i$ to thereby analytically determine the similarity.

(2) In case the detection pattern deviates significantly from a standard pattern as a function of concentration:

The whole region of concentration is divided into Q subregions r(where r=1, 2, ... or Q) so that the detected pattern is distinct in the subregions, wherein a set of detection patterns $\{\vec{p}_k{}^r\}$ (where k=1, 2, ... or $L^r$) are determined for Lr different concentrations in each subregion r as in the preceding case (1) and processed as a class through the procedure for analytically determining the similarity as described below.

Now, it is assumed that the N-dimensional detection pattern is represented by $\vec{x}$ and that a set of the N-dimensional patterns in number of $L^i$ which belongs to a class corresponding to a certain gas i is represented by $\{\vec{p}_k{}^i\}$ where k=1, 2, ... or $L^i$. On these conditions, the degree of similarity between the above class and the detection pattern $\vec{x}$ is defined as the function of the distance in the manner as follows:

$$S^i = \frac{1}{L^i} \sum_{k=1}^{L^i} \sum_{j=1}^{N} w^j (x_j - p^i_{kj})^2 \qquad (12)$$

where $S^i$ represents the degree of similarity, $x_j$ and $p_{kj}{}^i$ represent the j-th elements of the patterns $\vec{x}$ and $\vec{p}_k{}^i$, respectively, and $w^j$ represents a weight placed on the j-th elements. The weight $w^j$ is given by expression (13) mentioned below and represents intra-class clustering procedure, i.e. the procedure for transforming the set of the patterns belonging to a class into a more dense cluster.

$$w^j = \frac{1}{(\sigma^j)^2 \cdot \sum_{j=1}^{N} \frac{1}{(\sigma^j)^2}} \qquad (13)$$

where $\sigma^j$ represents dispersion and is given by $$(\sigma^j)^2 = \left\{ \frac{1}{L^i} \sum_{k=1}^{L^i} (p^i_{kj})^2 - \left( \frac{1}{L^i} \sum_{k=1}^{L^i} p^i_{kj} \right)^2 \right\} \qquad (14)$$

Thus, the following condition is satisfied.

$$\sum_{j=1}^{N} w^j = 1 \qquad (15)$$

When i is determined which satisfies the condition (16) for the similarity $S^i$ derived from the expression (12), that is, $$S \min = \min_i \{S^i\} \qquad (16)$$

the gas which comes to contact with the sensor element can be identified as the gas which belongs to the i-th class.

Once the sort or species of gas is identified, it is easy to derive the concentration of that gas by analyzing the detection signal output from the sensor element which exhibits relatively the highest sensitivity to the detected gas. As will be appreciated from the foregoing discussion, it is possible to identify qualitatively and quantitatively a given number of gases independent of the number of the incorporated gas sensor elements by appropriately selecting the detection characteristics of the sensor elements, so far as the detection patterns obtained upon detection of gases can be technically made to be distinctively peculiar to the gases to be detected.

Exemplary Embodiments of the Invention

In the following, exemplary embodiments of the present invention will be described in detail by referring to the drawings. The contents of description are as follows:

Example 1: In a gas detecting apparatus incorporating a sensor unit composed of three sensor elements, a method of manufacturing the sensor unit, establishment of gas detection characteristics, and method and apparatus for arithmetic processing.

Example 2: In a detecting apparatus for detecting odor and organic solvent vapor by using a sensor unit composed of six sensor elements, method of manufacturing the sensor unit, establishment of gas detection characteristics, and method and apparatus for arithmetic processing.

Example 3: Another example of the arithmetic processings which can be adopted in the Examples 1 and 2.

Example 4: Implementation of learning function in the odor/organic solvent vapor detecting apparatus according to the Example 2.

Example 1

1-1. Preparation of Paste

Three kinds of sensor materials, i.e. $SnO_2$, $WO_3$ and $LaNiO_3$ (lanthanum nickel oxide) were used for constituting the sensor unit for the gas detecting apparatus in the instant example. The material $WO_3$ is effective for detecting carbon monoxide, while $LaNiO_3$ is effective for detecting alcohol vapor. Concerning the detection characteristic of $LaNiO_3$, it should be added that when this material is exposed to a gas of high reducing power such as alcohol vapor under heating at ca. 300° C., the composition is deprived of oxygen, resulting in breakage of link M-O-M and reduction in the electric conductivity. When the alcohol vapor is removed, the material resumes the original composition ($LaNiO_3$) again to restore the initial electric conductivity ($G_0$). As another characteristic of $LaNiO_3$, it should be mentioned that the above phenomenon makes appearance in response to the presence of only alcohol vapor, and no reaction is exhibited by $LaNiO_3$ in response to such gases as hydrogen, methane, propane, isobutane, carbon monoxide and the like. For these reasons, $LaNiO_3$ can be effectively used as the material for the alcohol vapor detecting sensor element in practical applications.

1-1-1. Preparation Of $LaNiO_3$-Paste

Condensed and dry-solidified acetates of La and Ni were thermally decomposed at 600° C. in the air and fired at 1000° C. in the air to produce a polycrystalline solid material having the composition of $LaNiO_3$. This material was pulverized to obtain a finely pulverized black powder of $LaNiO_3$. Finely pulverized $LaNiO_3$ of 10 g was added with 6 cc of an organic vehicle and ca. 10% by weight (wt. %) of a crystalized glass of Si-Pd-Zn-Ti series and mixed intimately to form a paste of $LaNiO_3$.

1-1-2. Preparation Of WO$_3$-Paste 18 g of WO$_3$ pulverized to less than 1 μm in particle size and having purity of 99.99% was added with 0.2 g of Pd powder, 2 g of a binder glass and 7 cc of 9%-tridecanol solution of 10 cps ethyl cellulose and mixed intimately to prepare the gas-sensitive WO$_3$-paste

1-1-3. Preparation Of SnO$_2$-Paste

Metallic tin (Sn) having a purity of 99.99% was treated with concentrated nitric acid. After rinsing, white sediment of stannic acid was subjected to vaporization, soldified in dry state and pulverized, which was followed by firing in the air at 700° C. to obtain powder of SnO$_2$. This powder was added with aqueous solution of PdCl$_2$ and mixed intimately to obtain a powder mixture of SnO$_2$ and 1% of Pd. The powder mixture is treated in the same manner as in the case of the preparation of LaNiO$_3$-paste described above to obtain the gas sensitive SnO$_2$-paste.

1-2. Structure Of Sensor

Description will be made of a gas detecting sensor unit (also referred to simply as the sensor unit) which is implemented by using three types of the gas-sensitive pastes prepared in the manners mentioned above.

Figure 3:
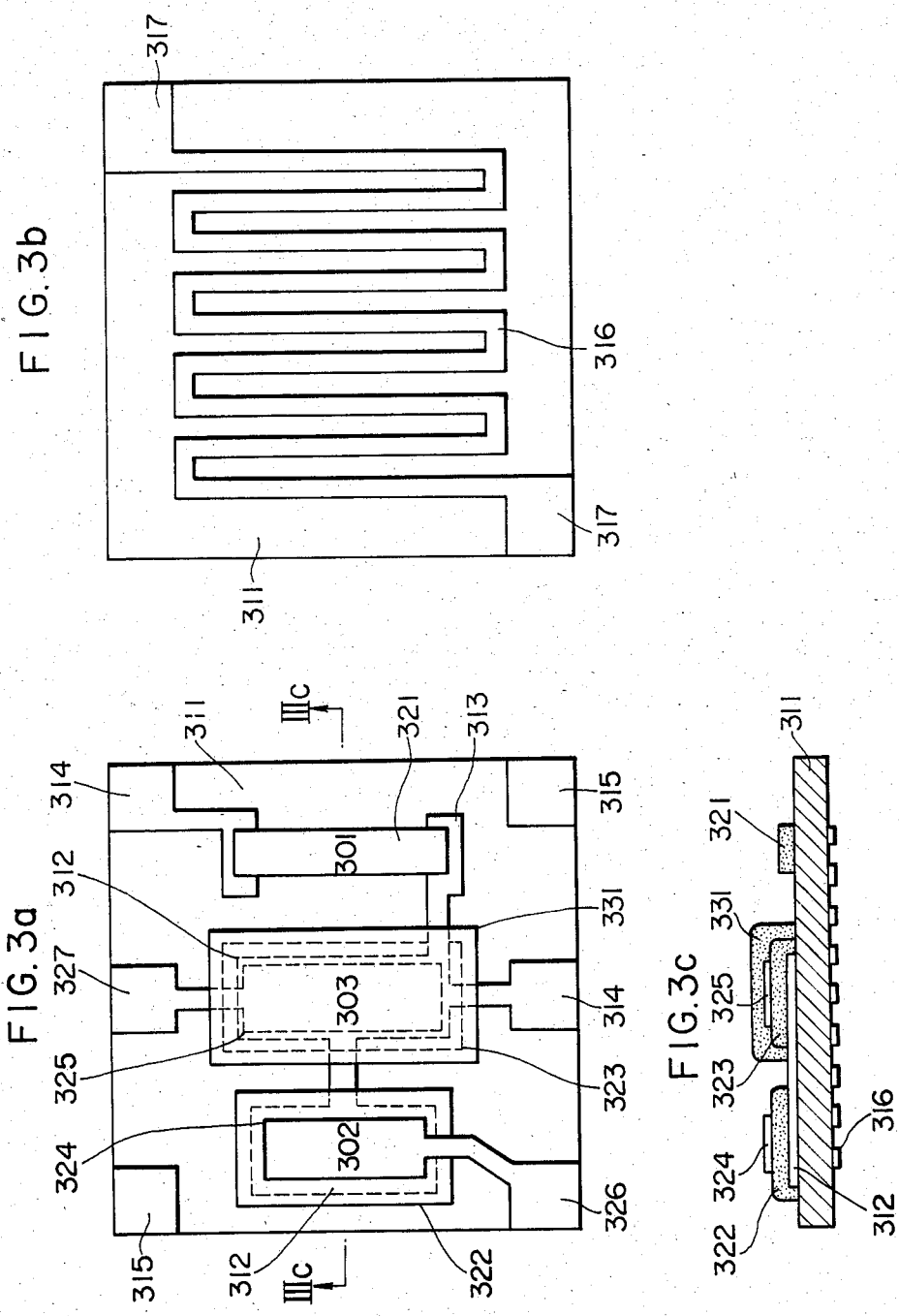

FIGS. 3a to 3c are views showing schematically a structure of a sensor unit which constitutes the main part of the gas detecting apparatus according to the instant exemplary embodiment, wherein FIG. 3a is a top plan view, FIG. 3b is a bottom plan view and FIG. 3b is a sectional view taken along the line IIIc—IIIc in FIG. 3a. As is shown in FIG. 3a, three gas detecting elements (also referred to as sensor element or simply sensor) 301, 302 and 303 are provided which are constituted by the aforementioned pastes of LaNiO$_3$, WO$_3$ and SnO$_2$, respectively. Describing the process in which the individual sensor elements were realized, a common refractory insulating substrate 311 was first deposited with lower electrodes 312 and interconnecting conductors 313 and 314 at respective predetermined locations by using a gold-conductor paste (e.g. paste No. 8760 manufactured by E. I. du Pont de Nemours & Co.) through a well known thick film printing technology. Concurrently, a heater pattern 316 was formed on the rear surface of the refractory insulating substrate 311 by using a gold-conductor paste (e.g. the above cited paste No. 87600), as is shown in FIG. 3b. The assembly thus prepared was fired at a temperature of 1200° C. for two hours to prepare a substrate for the sensor unit. Subsequently, LaNiO$_3$-paste 321, WO$_3$-paste 322 and SnO$_2$-paste 323 were deposited at respective predetermined locations by a thick film printing process similar to that adopted in forming the lower electrodes 312, etc., and dried. Subsequently, upper electrodes 324 and 325 are deposited in predetermined configuration through a printing process by using a gold-conductor paste (e.g. above cited paste No. 8760) and dried. The assembly was fired at a firing temperature of 900° C. for ten minutes. Additionally, a filter was provided for the sensor element 303. To this end, the LaNiO$_3$-paste mentioned above was used as the filter material to print a filter 331 at a predetermined location relative to the sensor element 303, and fired at a temperature of 900° C. for ten minutes after having been dried. In this way, a sensor unit of a sandwich structure or a sheet-like structure is finished.

1-3. Gas Detection Characteristics

Next description will be made concerning the gas detection characteristics of the sensor unit.

Figure 4:
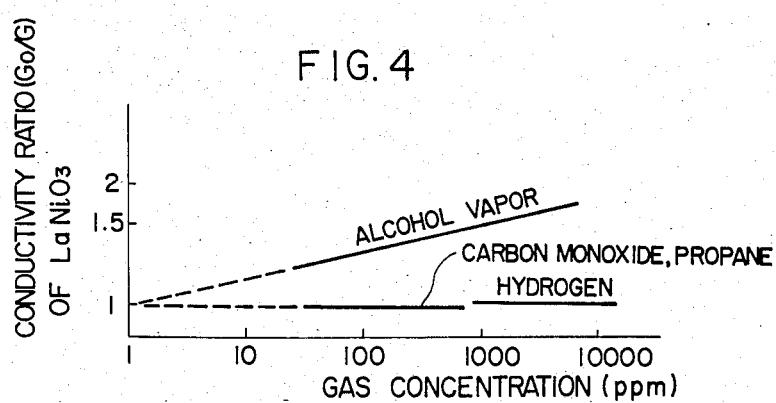
FIGS. 4 to 6 are views showing detection characteristics as actually measured for individual gases.
Figure 5:
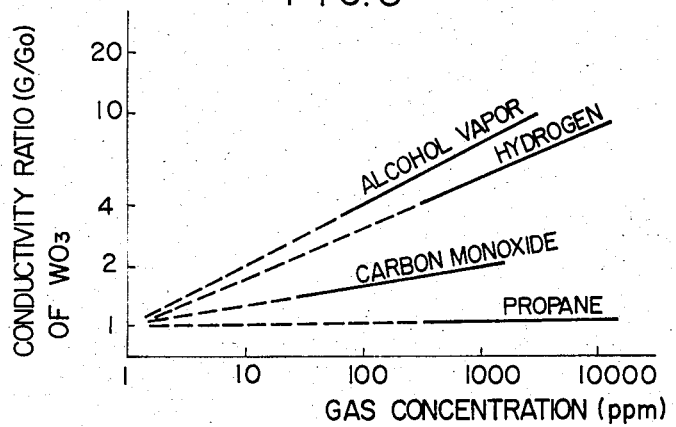
Figure 6:
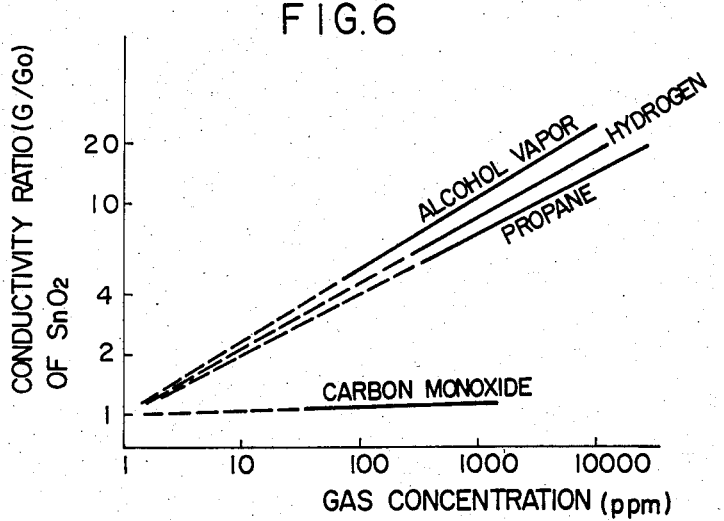

FIG. 4 graphically illustrates the characteristics of the LaNiO$_3$ sensor element. It will be seen that the LaNiO$_3$ sensor element is sensitive to only alcohol vapor and does not respond to the presence of carbon monoxide, propane and hydrogen gases. In view of the fact that the LaNiO$_3$-sensor element is a P-type semiconductor whose conductivity is decreased upon detection of alcohol vapor, the conductivity ratio $G_0/G$ (namcly, reciprocal of $G/G_0$) is taken along the ordinate in terms of logarithmic values for convenience' sake. FIGS. 5 and 6 show graphically the corresponding characteristics of the WO$_3$-sensor element and the SnO$_2$-sensor element, respectively.

It should be mentioned that substantial linearity of the characteristic curves shown in FIGS. 4 to 6 is ascribed to the fact that data obtained through measurement were processed in accordance with the expression (4) described hereinbefore.

Figure 16:
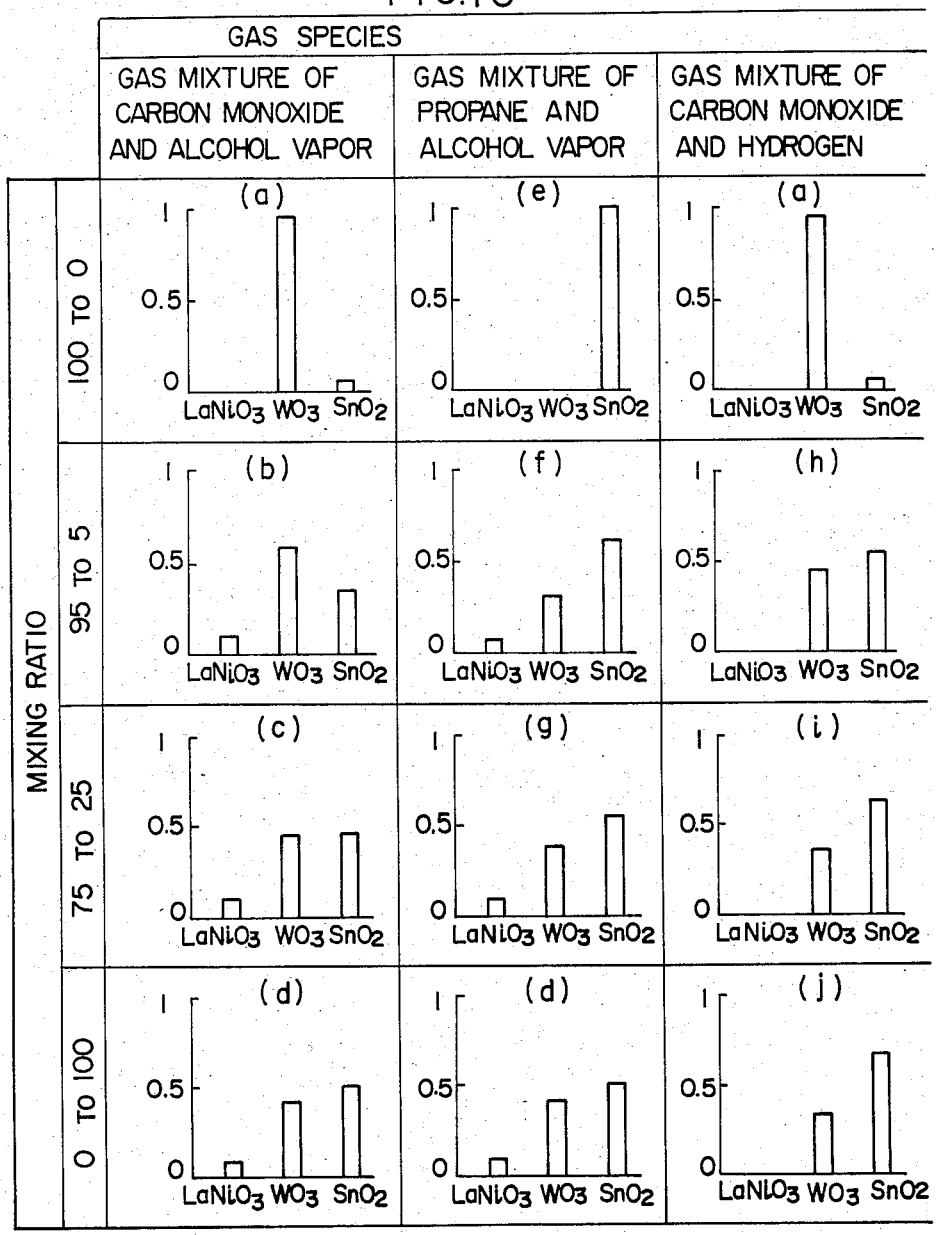
FIG. 16 is a view showing standard patterns derived from the actually measured data shown in FIGS. 4 to 15.

On the basis of the characteristic data illustrated in FIGS. 4 to 6, standard patterns for carbon monoxide, propane, hydrogen and alcohol vapor, respectively, were determined which are shown in FIG. 16 at (a), (e), (j) and (d), respectively.

Further, standard patterns for gas mixtures were determined for three combinations of carbon monoxide and alcohol vapor, propane and alcohol vapor, and carbon monoxide and hdyrogen, by way of example. More particularly, the gas detection characteristics of the sensor elements for these gas mixtures were measured with the mixing ratios being used as parameters for arithmetically determining the corresponding standard patterns as mentioned below.

Figure 7:
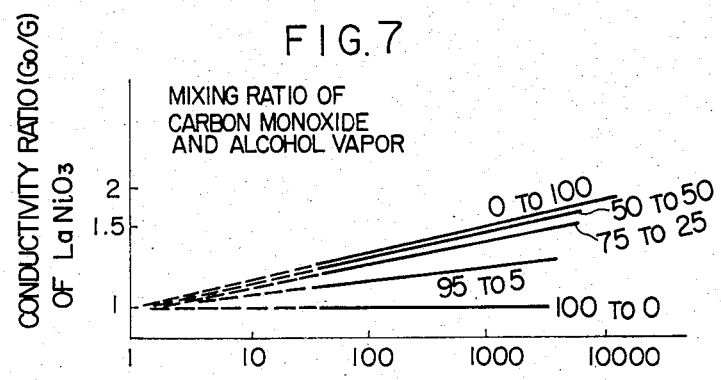
FIGS. 7 to 15 are views illustrating detection characteristics as actually measured for gas mixtures with mixing ratios being used as parameters.
Figure 8:
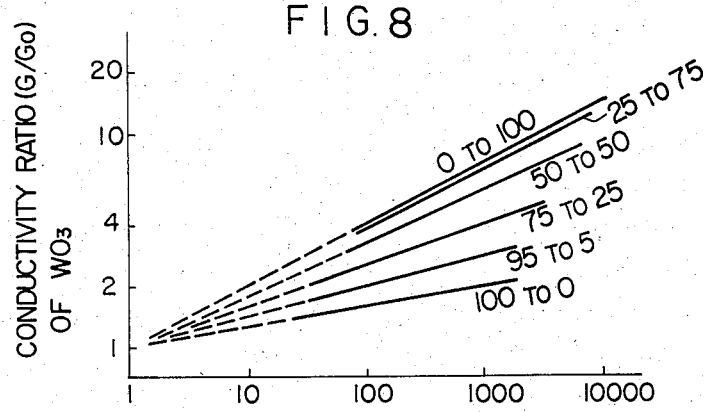
Figure 9:
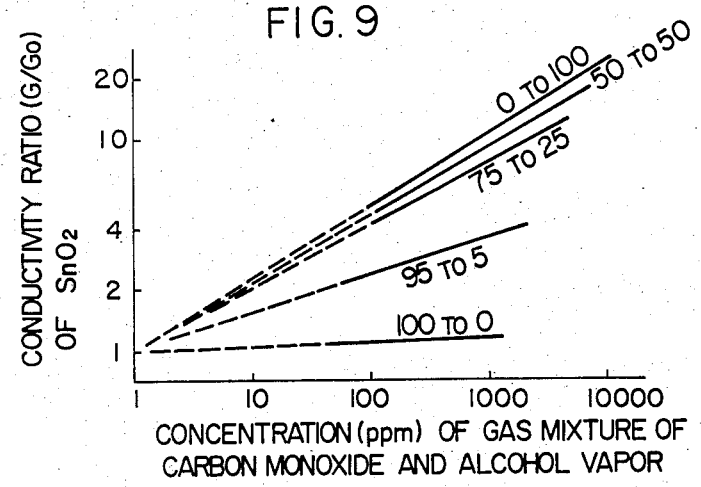

In the first place, description will be made as to how the standard pattern for the gas mixture of carbon monoxide and alcohol vapor was derived from the gas detection characteristic data with the mixing ratio being used as parameter. As will be seen in FIGS. 7 and 9, the gas detection characteristics of the three sensor elements vary in dependence on the mixing ratio. With a view to obtaining the standard patterns which exhibit as significant characteristics as possible, standard patterns were derived for two species of gas mixtures which contain, respectively, 95 parts of carbon monoxide and 5 parts of alcohol vapor, and 75 parts of carbon monoxide and 25 parts of alcohol vapor in the instant example. The standard patterns as obtained are such as those shown in FIG. 16 at (b) and (c), respectively.

Figure 10:
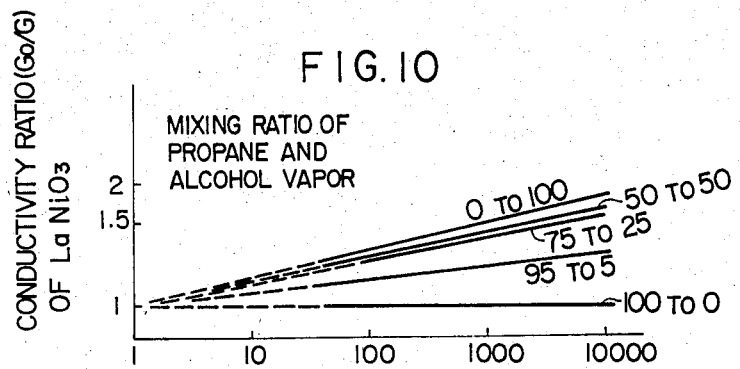
Figure 11:
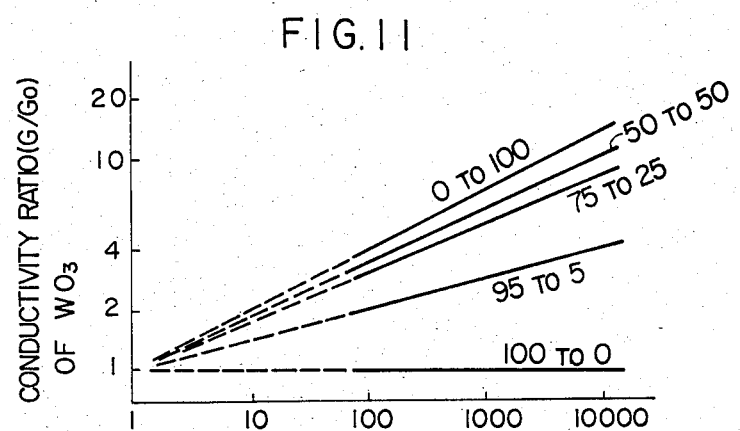
Figure 12:
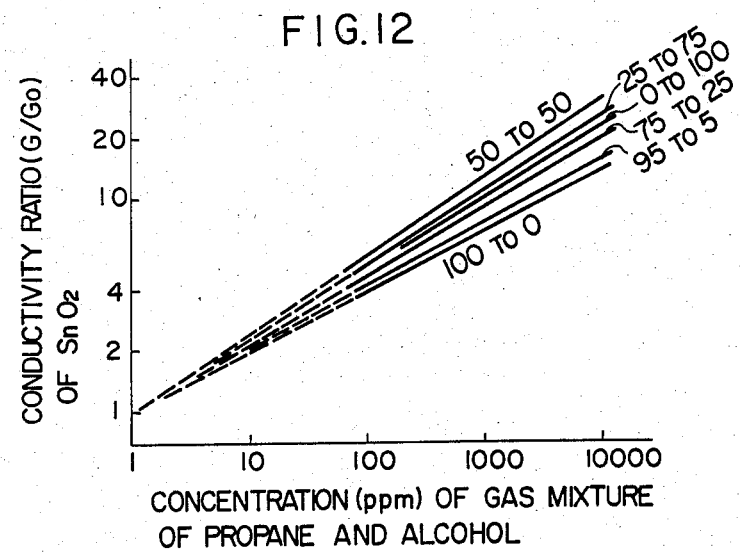

The gas detection characteristics of the three sensor elements for the gas mixture of propane and alcohol vapor are such as those shown in FIGS. 10 to 12, respectively. The standard patterns for the gas mixtures containing propane and alcohol at the mixing ratios of 95 to 5 and 75 to 25 are such as those shown in FIG. 16 at (f) and (g), respectively.

Figure 13:
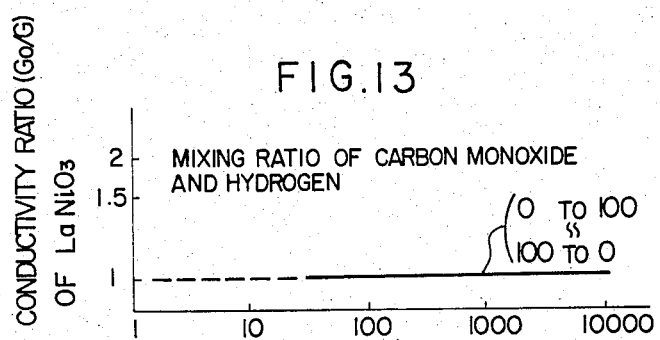
Figure 14:
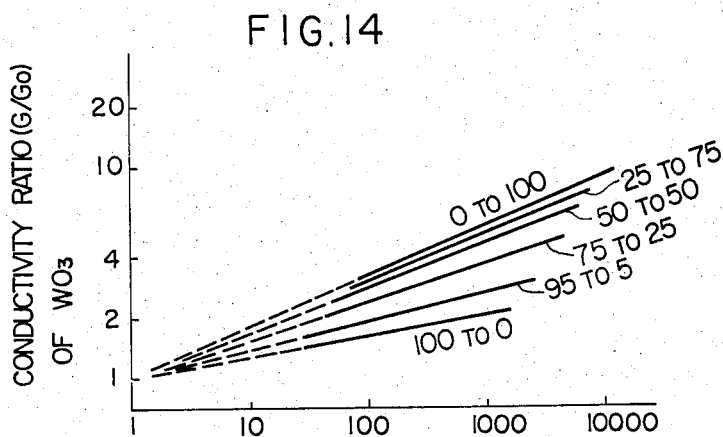
Figure 15:
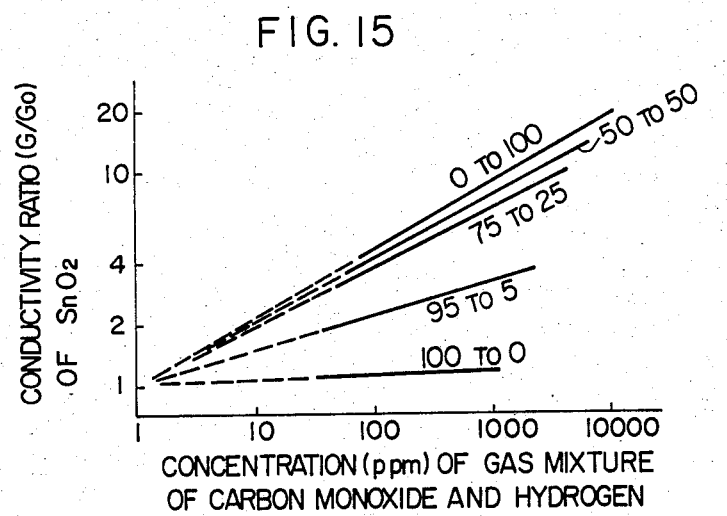

Similarly, the gas detection characteristics of the three sensor elements for the gas mixture of carbon monoxide and hydrogen are shown in FIGS. 13 to 15, respectively. The standard patterns for the gas mixture containing carbon monoxide and hydrogen at the ratios of 95 to 5 and 75 to 25, respectively, are shown in FIG. 16 at (h) and (i), respectively.

1-4. Qualitative And Quantitative Analyses Of Gases

The ten standard patterns thus derived were classified into ten classes, respectively. Since the patterns for the gas mixtures undergo more or less variations in dependence on the gas concentration, the number of the standard patterns for the classes to which the gas mixtures belong, respectively, was increased by three to seven. The weights imparted to the classes were calculated in accordance with the expression (13) described hereinbefore. In the table 1, there are listed the standard patterns belonging to the respective classes together with the assigned weights.

TABLE 1

| Class | Gas Species | Standard Pattern | | | Weight | | |
|---|---|---|---|---|---|---|---|
| | | $LaNiO_3$ | $WO_3$ | $SnO_2$ | $LaNiO_3$ | $WO_3$ | $SnO_2$ |
| 1 | carbon monoxide | 0 | 0.95 | 0.05 | 0.333 | 0.333 | 0.333 |
| 2 | propane | 0 | 0 | 1 | 0.333 | 0.333 | 0.333 |
| 3 | hydrogen | 0 | 0.33 | 0.67 | 0.333 | 0.333 | 0.333 |
| 4 | alcohol vapor | 0.07 | 0.32 | 0.61 | 0.333 | 0.333 | 0.333 |
| 5 | gas mixture of 95 parts of CO and 5 parts of alcohol vapor | 0.06 0.08 0.09 0.11 0.10 0.10 | 0.60 0.60 0.63 0.58 0.61 0.59 | 0.34 0.32 0.28 0.31 0.29 0.31 | 0.360 | 0.388 | 0.252 |
| 6 | gas mixture of 75 parts of CO and 25 parts of alcohol vapor | 0.08 0.10 0.07 0.09 0.11 0.13 0.14 | 0.47 0.46 0.47 0.44 0.43 0.45 0.43 | 0.45 0.44 0.46 0.47 0.46 0.42 0.43 | 0.192 | 0.420 | 0.388 |
| 7 | gas mixture of 95 parts of propane and 5 parts of alcohol vapor | 0.05 0.07 0.06 0.08 0.11 0.09 | 0.28 0.26 0.29 0.27 0.23 0.27 | 0.67 0.67 0.65 0.65 0.66 0.64 | 0.190 | 0.207 | 0.603 |
| 8 | gas mixture of 75 parts of propane and 25 parts of alcohol vapor | 0.08 0.09 0.08 0.10 0.11 0.12 | 0.39 0.36 0.35 0.36 0.35 0.33 | 0.53 0.55 0.57 0.54 0.54 0.55 | 0.303 | 0.171 | 0.526 |
| 9 | gas mixture of 95 parts of CO and 5 parts of $H_2$ | 0 0 0 | 0.45 0.44 0.48 | 0.55 0.56 0.52 | 0.333 | 0.333 | 0.333 |
| 10 | gas mixture of 75 parts of CO and 25 parts of $H_2$ | 0 0 0 0 0 | 0.37 0.40 0.39 0.41 0.38 | 0.63 0.60 0.61 0.59 0.62 | 0.333 | 0.333 | 0.333 |

TABLE 2

| Example of calculation | Gas concentration (ppm) | | | | Detection pattern | | | Degree of similarity (minimum value in ellipse) | | | | | |
|---|---|---|---|---|---|---|---|---|---|---|---|---|---|
| | Carbon monoxide | Propane | Hydrogen | Alcohol vapor | $LaNiO_3$ | $WO_3$ | $SnO_2$ | $S^1$ | $S^2$ | $S^3$ | $S^4$ | $S^5$ | $S^6$ |
| 1 | 200 | 0 | 0 | 0 | 0.00 | 0.92 | 0.08 | (0.0006) | 0.5637 | 0.2318 | 0.2151 | 0.0557 | 0.1474 |
| 2 | 0 | 3000 | 0 | 0 | 0.00 | 0.02 | 0.98 | 0.5760 | (0.0003) | 0.0640 | 0.0772 | 0.2482 | 0.1902 |
| 3 | 0 | 0 | 2000 | 0 | 0.00 | 0.29 | 0.71 | 0.2901 | 0.0560 | (0.0011) | 0.0053 | 0.0815 | 0.0399 |
| 4 | 0 | 0 | 0 | 1000 | 0.07 | 0.31 | 0.62 | 0.2462 | 0.0817 | 0.0026 | (0.0001) | 0.0579 | 0.0204 |
| 5 | 0 | 0 | 0 | 2000 | 0.09 | 0.32 | 0.59 | 0.2320 | 0.0928 | 0.0049 | (0.0003) | 0.0511 | 0.0154 |
| 6 | 500 | 0 | 0 | 50 | 0.07 | 0.61 | 0.32 | 0.0644 | 0.2795 | 0.0685 | 0.0560 | (0.0005) | 0.0176 |
| 7 | 400 | 0 | 0 | 50 | 0.10 | 0.63 | 0.27 | 0.0535 | 0.3130 | 0.0866 | 0.0708 | (0.0010) | 0.0261 |
| 8 | 250 | 0 | 0 | 50 | 0.07 | 0.49 | 0.44 | 0.1227 | 0.1860 | 0.0278 | 0.0192 | 0.0096 | (0.0012) |
| 9 | 100 | 0 | 0 | 50 | 0.13 | 0.42 | 0.45 | 0.1524 | 0.1651 | 0.0244 | 0.0131 | 0.0187 | (0.0008) |
| 10 | 200 | 0 | 0 | 50 | 0.09 | 0.47 | 0.44 | 0.1301 | 0.1807 | 0.0268 | 0.0172 | 0.0114 | (0.0005) |
| 11 | 150 | 0 | 0 | 50 | 0.12 | 0.47 | 0.41 | 0.1247 | 0.1943 | 0.0338 | 0.0216 | 0.0099 | (0.0011) |
| 12 | 0 | 2000 | 0 | 200 | 0.07 | 0.27 | 0.66 | 0.2795 | 0.0644 | 0.0029 | 0.0017 | 0.0743 | 0.0317 |
| 13 | 0 | 1000 | 0 | 100 | 0.10 | 0.24 | 0.66 | 0.2951 | 0.0610 | 0.0061 | 0.0033 | 0.0822 | 0.0364 |
| 14 | 0 | 3000 | 0 | 1000 | 0.09 | 0.36 | 0.55 | 0.2019 | 0.1133 | 0.0078 | 0.0019 | 0.0377 | 0.0079 |
| 15 | 0 | 1500 | 0 | 500 | 0.10 | 0.39 | 0.51 | 0.1782 | 0.1339 | 0.0131 | 0.0053 | 0.0280 | 0.0034 |
| 16 | 0 | 1000 | 0 | 300 | 0.13 | 0.35 | 0.52 | 0.1991 | 0.1231 | 0.0133 | 0.0042 | 0.0367 | 0.0067 |
| 17 | 0 | 1200 | 0 | 300 | 0.12 | 0.35 | 0.53 | 0.2014 | 0.1191 | 0.0115 | 0.0033 | 0.0376 | 0.0072 |
| 18 | 500 | 0 | 50 | 0 | 0.00 | 0.47 | 0.53 | 0.1534 | 0.1471 | 0.0131 | 0.0113 | 0.0223 | 0.0052 |
| 19 | 300 | 0 | 100 | 0 | 0.00 | 0.38 | 0.62 | 0.2164 | 0.0962 | 0.0017 | 0.0029 | 0.0467 | 0.0160 |
| 20 | 400 | 0 | 100 | 0 | 0.00 | 0.40 | 0.60 | 0.2015 | 0.1066 | 0.0033 | 0.0038 | 0.0404 | 0.0125 |

| Example of calculation | Degree of similarity (minimum value in ellipse) | | | | Class Estimated/Actual |
|---|---|---|---|---|---|
| | $S^7$ | $S^8$ | $S^9$ | $S^{10}$ | |
| 1 | 0.2902 | 0.1719 | 0.1432 | 0.1872 | 1/1 |

TABLE 2-continued

|    |          |          |          |          |       |
|----|----------|----------|----------|----------|-------|
| 2  | 0.0770   | 0.1212   | 0.1272   | 0.0913   | 2/2   |
| 3  | 0.0032   | 0.0178   | 0.0187   | 0.0068   | 3/3   |
| 4  | 0.0014   | 0.0036   | 0.0109   | 0.0039   | 4/4   |
| 5  | 0.0035   | 0.0014   | 0.0098   | 0.0046   | 4/4   |
| 6  | 0.0930   | 0.0384   | 0.0263   | 0.0459   | 5/5   |
| 7  | 0.1178   | 0.0532   | 0.0384   | 0.0611   | 5/5   |
| 8  | 0.0389   | 0.0094   | 0.0057   | 0.0147   | 6/6   |
| 9  | 0.0314   | 0.0061   | 0.0092   | 0.0146   | 6/6   |
| 10 | 0.0371   | 0.0084   | 0.0065   | 0.0146   | 6/6   |
| 11 | 0.0458   | 0.0124   | 0.0110   | 0.0204   | 6/6   |
| 12 | (0.0002) | 0.0085   | 0.0180   | 0.0074   | 7/7   |
| 13 | (0.0005) | 0.0093   | 0.0237   | 0.0118   | 7/7   |
| 14 | 0.0089   | (0.0002) | 0.0060   | 0.0043   | 8/8   |
| 15 | 0.0164   | (0.0011) | 0.0054   | 0.0068   | 8/8   |
| 16 | 0.0135   | (0.0009) | 0.0098   | 0.0090   | 8/8   |
| 17 | 0.0117   | (0.0005) | 0.0088   | 0.0076   | 8/8   |
| 18 | 0.0196   | 0.0054   | (0.0003) | 0.0044   | 9/9   |
| 19 | 0.0048   | 0.0060   | 0.0041   | (0.0002) | 10/10 |
| 20 | 0.0070   | 0.0049   | 0.0023   | (0.0002) | 10/10 |

Results of calculations effected on trial for the identification of given gases on the basis of the classes prepared in the manner mentioned above are listed in the table 2. The examples of calculations numbered twenty. In each of the calculations, electrical conductivities of the sensor elements $LaNiO_3$, $WO_3$ and $SnO_2$ exposed to each of carbon monoxide, propane, hydrogen and alcohol vapor solely and gas mixtures thereof were measured. On the basis of the results of measurements, the corresponding detection patterns were determined through calculation in accordance with the expression (6). Next, the degrees of similarity of these detection patterns to the ten classes were arithmetically determined. Subsequently, the class which has minimum value in the degree of similarity was selectively extracted to determine the presence of coincidence between the class thus estimated and the class identified on the basis of the gas concentrations actually measured. As will be seen in the table 2, there exist coincidence between the estimated classes and the actually identified classes in all of the twenty examples. In particular, significant difference is observed between the similarities calculated for carbon monoxide and propane, respectively.

It goes without saying that so far as the class to which the gas to be detected belongs can be estimated, i.e. so far as the detected gas can be identified, the concentration of the detected gas can be quantitatively determined on the basis of the detection data available from the particular sensor element which exhibits the highest sensitivity to the identified gas.

5-1. Structure Of Apparatus

In this section, description is made of a structure of the gas detecting apparatus incorporating the aforementioned sensor unit and a method of arithmetically processing the detection signals produced by the sensor unit.

1-5-1. Processing Circuit

Figure 17:
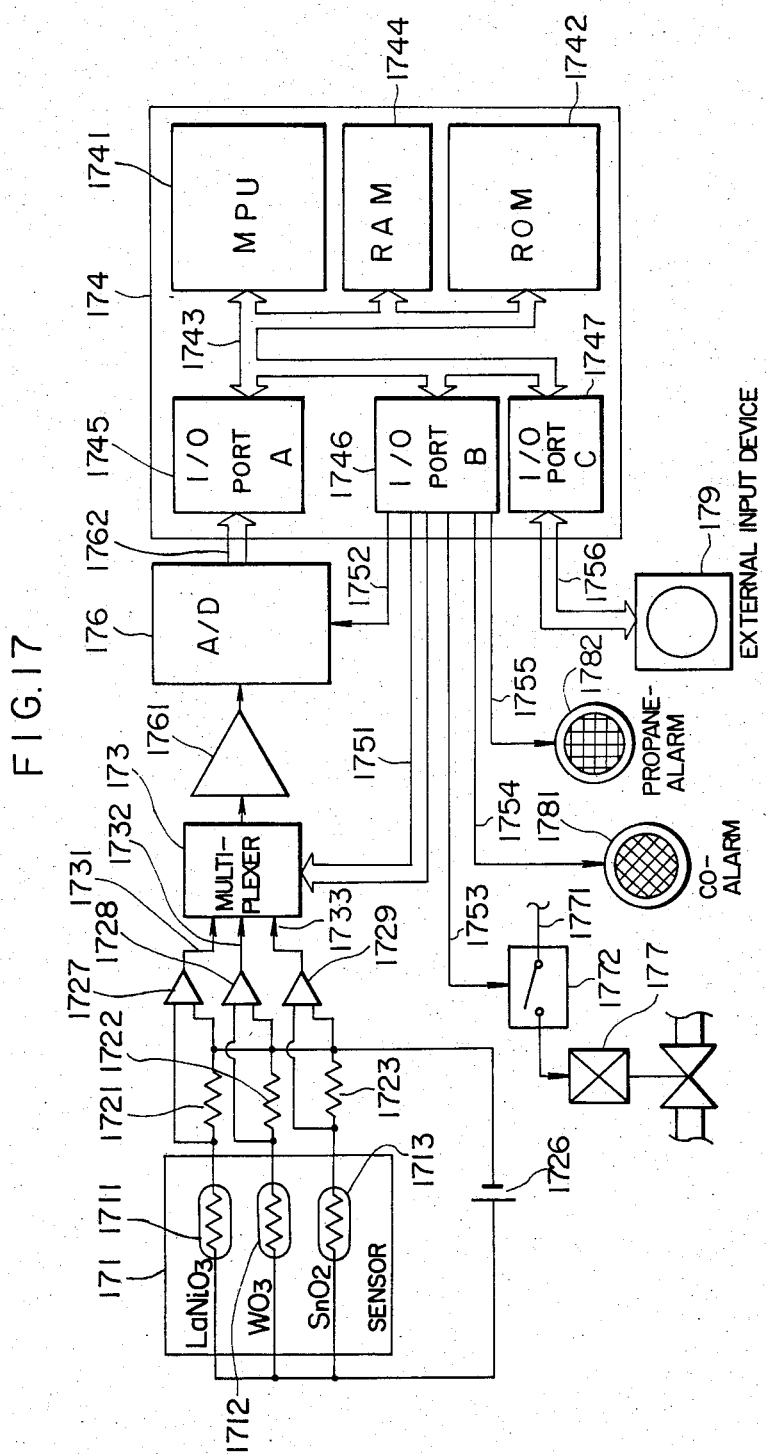
FIG. 17 is a schematic circuit diagram showing an arithmetic processing circuit of the gas detecting apparatus according to a first exemplary embodiment of the invention.

FIG. 17 is a view showing a general arrangement of the gas detecting apparatus according to an embodiment of the present invention. The sensor unit 171, powered by battery 1726, includes three sensor elements 1711 (301), 1712 (302) and 1713 (303) constituted, respectively, by $LaNiO_3$, $WO_3$ and $SnO_2$ described above. Fixed resistors 1721, 1722 and 1723 are connected in series to the sensor elements 1721, 1722 and 1723, respectively. Voltage drops appearing across these resistors are appropriately amplified by operational amplifiers 1727, 1728 and 1729 to obtain analog signals 1731, 1732 and 1733, respectively. These analog signals are selectively gated through a multiplexer 173 operating in response to a control signal 1751 supplied from a microcomputer 174, and after having been amplified by an operational amplifier 1761, supplied to an analog-to-digital (A/D) converter 176 to be converted into digital signals 1762, the A/D converter being controlled by a control signal 1752 produced by the microcomputer 174. The arithmetic processing of the digital signal 1762 will hereinafter be described in greater detail. The microcomputer 174 includes a processor unit (MPU) 1741, a random access memory (RAM) 1744, a read-only memory (ROM) 1742, a signal bus line 1743 and input/output (I/0) ports 1745, 1746 and 1747 for executing arithmetic processings mentioned hereinafter.

Commands for interruption of gas supply path, generation of alarm and the like produced in dependence on the results of the arithmetic operations performed by the microcomputer 174 are outputted in the form of control signals 1753, 1754 and 1755. More particularly, the control signal 1753 controls ON-OFF operation of an electromagnetic relay 1772 of a power supply circuit 1771 provided for driving the gas supply intercepting valve 177 in such a manner in which the intercept valve 177 is normally opened and closed upon detection of gas leakage. On the other hand, the control signal 1754 triggers operation of a CO-alarm buzzer 1781 upon detection of carbon monoxide, while the control signal 1755 serves to energize a propane alarm buzzer 1782 when leakage of propane is detected.

Changes of gas species to be detected as well as alteration of concentration can be readily realized by preparing corresponding control signals with the aid of external input means 179, the control signals being supplied to the microcoputer 174 through the bus line 1756.

1-5-2. Flow Chart For Arithmetic Processings

Figure 18A:
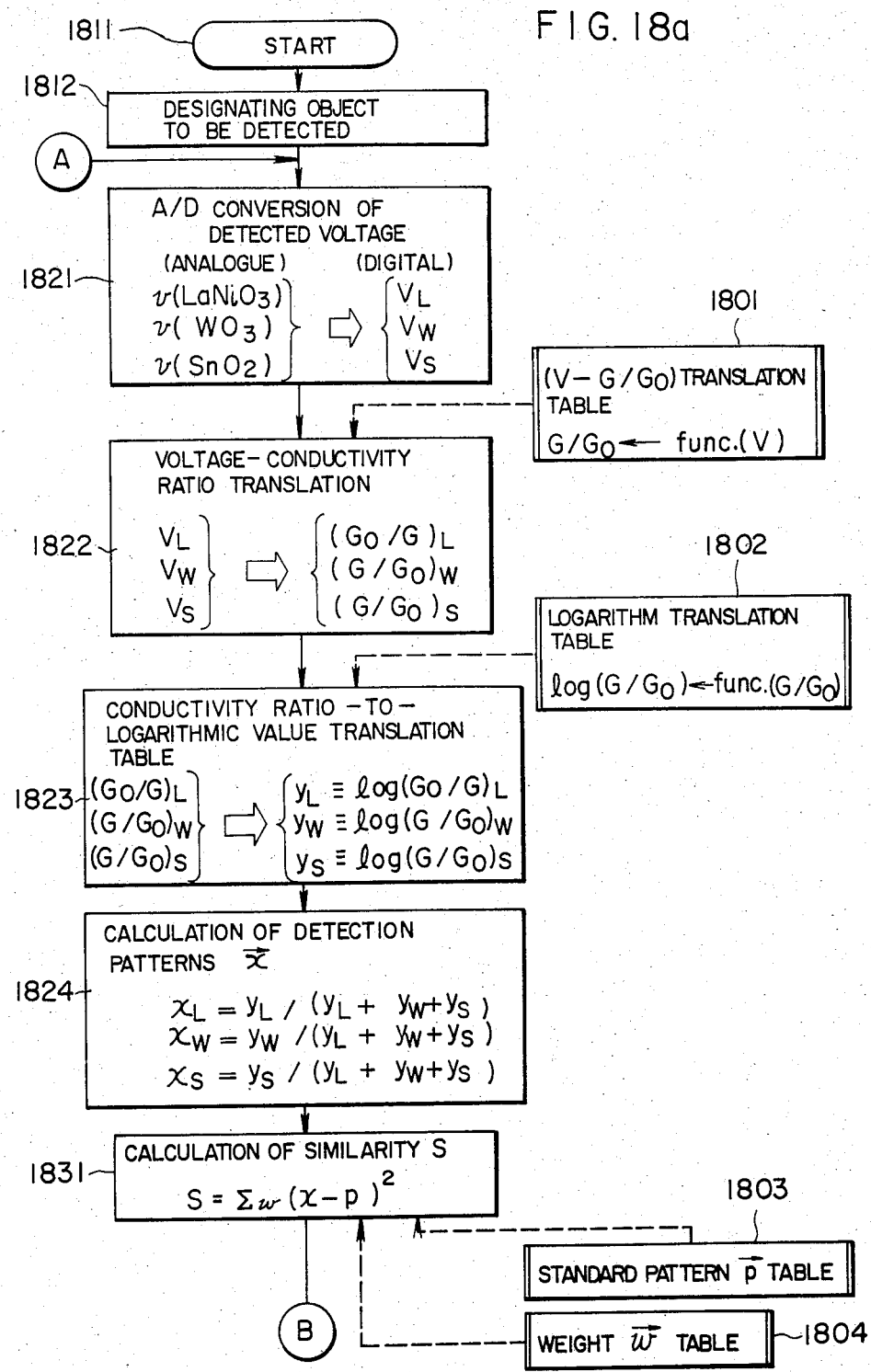
FIGS. 18a and 18b show a flow chart for illustrating arithmetic processing procedures executed by the processing circuit according to the first embodiment of the invention.

A typical operation program executed by the microcomputer 174 will be described by referring to FIGS. 18a and b. At a step 1811, start is commanded. At a step 1812, objects to be detected are designated with the aid of the external input device 179. More specifically, species of gases to be detected, concentration of a desired gas contained in a gas mixture or the like is specified at the step 1821 in dependence on practical applications for which the gas detecting apparatus is intended to be used. The information concerning the specification or designation of the objects to be detected is stored in the RAM 1744 through the I/O port 1747 and the signal bus line 1743.

At a succeeding step 1821, A/D conversion of the detection voltages of three sensors LaNiO$_3$, WO$_3$ and SnO$_2$ is effected by controlling the multiplexer 173 and the A/D converter 176, whereby digital values $V_L$, $V_W$ and $V_S$ each of 10 bits are derived from the average values of the result of the A/D conversion of the analog output voltages produced by the three sensor elements, respectively. On the basis of these digital values and numerical values cited from voltage-to-conductivity ratio translation table 1801 stored previously in the ROM 1742, translation of voltage-to-conductivity ratio is carried out at a step 1822. In this connection, argument of the translation table is determined on the basis of the most significant 6 bits of the digital value $V_L$, $V_W$ or $V_S$ in accordance with $$A = \text{(leading address of translation table)} + \text{(more significant 6 bits of digital value)} \times 2 \quad (17)$$

Data corresponding to this argument is located at addresses A and A+1 over two bytes and has a format given by the following internal code:

$$\text{DATA} = u \cdot 2^v \quad (18)$$

where u represents mantissa part (11-bit binary number with sign) and v represents exponent part (5-bit binary number with sign).

Further, by using of less significant four bits of the digital value, linear interpolation is performed on the basis of data at A and A+1 and data at A+2 and A+3 in accordance with the below mentioned expression (19) to arithmetically determine the conductivity ratio $G/G_0$.

$$G/G_0 = \frac{\text{less significant 4 bits}}{2^4} \{(A+2 : A+3) - (A : A+1)\} + (A : A+1) \quad (19)$$

Subsequently, the 10-bit value of the conductivity ratio is divided into the 6-bit part and the 4-bit part, and conductivity ratio-to-logarithm translation is effected at a step 1823 by referring to a logarithm translation table 1802 previously stored in the ROM 1742, to derive log $(G/G_0)_S$, etc. Subsequently, a step 1824 is executed to determine the detection patterns $\vec{x}$ in accordance with $$X_x = \frac{Y_x}{Y_L + Y_W + Y_S}, \quad (x = L, W, S) \quad (20)$$

where $Y_x = \log (G/G_0)_x$.

Next, appropriate numerical values are cited from a standard pattern $\vec{(p)}$ table 1803 and a weight $\vec{(w)}$ table 1802 stored in the ROM 1742, and degrees of similarity between the detection pattern x determined arithmetically as mentioned above and the classes are calculated in accordance with the below mentioned expression (21) at a step 1831, which is followed by the execution of a step 1832 for identifying the gas species by determining the minimum degree of similarity $S_{min}$ in accordance with the below mentioned expression (22).

$$S_i = \sum_j w_{ij}(x_j - p_{ij})^2 \quad (21)$$

$$S_{min} = \min_i \{S_i\} \quad (22)$$

where $S_i$ represents the degree of similarity to the i-th standard pattern. Upon completion of the identification of the gas species, 10-bit value of the conductivity ratio determined for the sensor element whose output is to be utilized for the quantitative determination of concentration is divided into 6-bit part and 4-bit part, whereby an appropriate numerical value is cited from a concentration table 1805 stored in the ROM through the procedure similar to that for the determination of logarithmic value based on the conductivity ratio described above, to thereby execute the step 184 for determining concentration of the identified gas.

Finally, on the basis of the results of the identification of gas and the quantitative determination of concentration thereof as well as the aforementioned specific information placed in the RAM 1744, decision step 185 is executed for deciding whether the alarm or control is to be triggered or not. If this step results in "NO", execution is repeated starting from the step 1821. When the decision step 185 results in "YES", an alarm indicating the presence of carbon monoxide (step 1862), an alarm indicating the presence of propane (step 1863) or interruption of the gas supply path (step 1864) is brought about through an output control step 1861. The alarm or control can be sustained through a repetition control (step 187). The processing procedure described so far is again initiated starting from the step 1821.

By virtue of the structure of the gas detecting apparatus as well as the arithmetic processings described above, not only the quantitative determination of concentrations of carbon monoxide and propane can be carried out without being disturbed by alcohol vapor, but also the qualitative and quantitative identifications can be realized for a number of different gases which exceeds the number of the gas sensor elements incorporated in the gas detecting apparatus. Besides, the arithmetic processings required for the qualitative and quantitative identifications can be executed at a high speed on a real time basis. Thus, the invention provides great advantages over the hitherto known gas detecting apparatus in which semiconductor sensor elements are used.

Because a great variety of objects to be detected can be specified or designated with the aid of the external input device, change of gases to be detected as well as quantitative determination of concentration for the gas mixtures covering numerous combinations of gases used in various gas service systems can be dealt with simple manipulations of switches. Thus, the gas detecting apparatus according to the illustrated embodiment of the invention enjoys great advantages in respect to the universality of applications, mass production and others.

EXAMPLE 2

2-1. Preparation Of Pastes

Six types of materials, i.e. ZnO, ZnO+Pt (ZnO added with an appropriate amount of Pt, same holding true for the similar expressions appearing in the following), WO$_3$, WO$_3$+Pt, SnO$_2$ and SnO$_2$+Pd were prepared. Since the processes for preparing these six compositions are substantially same, description will be made only of the preparation of the pastes of ZnO and ZnO+Pt.

At first, commercially available ZnO-powder of 99.9% in purity manufactured by High Purity Chemical Lab. Inc. or ZnO-powder of 99.9% in purity manufactured by Rare Metallic Co.) was weighed in a proper amount. Particle size of this pulverized raw material was previously straightened. Subsequently, powder of Pt or $PtCl_2$ was added as a noble metal catalyst to the ZnO-powder in such an amount that Pt is equivalent to 1% of Zn in weight. The process of preparation is same in case the noble metal catalyst to be added is Pd. The above amount of catalyst is only for the illustrative purpose, and identical preparing process can be adopted in case the amount of catalyst to be added differs from the value mentioned above. Of course, no noble metal is added in the case of preparation of the ZnO-paste.

90 wt. % of the aforementioned pulverized starting material was added and mixed with 10 wt. % of a glass powder belonging to $PbO-TiO_2-SiO_2$ series. 10 g of this mixture was added and mixed intensively with 3 ml of one vehicle consisting of nitrocellulose α-terpineol to finish the gas-sensitive paste.

2-2. Structure of Sensor Unit

Description will now be made of the sensor unit constituted by six types of the gas-sensitive pastes prepared in the manner described above.

FIG. 19a is a plan view showing schematically the structure of the sensor unit according to the instant example, and FIG. 19b is a sectional view taken along the line XIXb—XIXb in FIG. 19a. The sensor unit includes six sensor elements 1901, 1902, . . . , 1906 constituted, respectively, by the six different gas-sensitive paste mentioned above. More particularly, a common refractory insulation substrate 191 is first provided with six lower electrodes 192 at predetermined positions by using a platinum conductor paste (e.g. paste "TR 760A" manufactured by Tanaka-Matthey Co.) simultaneously with deposition of interconnecting conductors 193 and 196 for the lower electrodes 192. After the pastes having been dried, the rear surface of the substrate is deposited with a pattern of heater by using a platinum conductor paste (e.g. the above mentioned TR 760A), and dried. The assembly is fired at a temperature of 1200° C. for two hours to thereby prepare the substrate for the sensor unit. Subsequently, six gas-sensitive pastes 1941 to 1946 are printed on the lower electrodes 192, respectively, in a predetermined thickness of ca. 50 μm. After the pastes having been dried, upper electrodes 195 and terminals 1951 to 1956 are deposited on the substrate in predetermined configurations by using a platinum paste (e.g. the above mentioned "TR 760A"), and dried. The assembly is subsequently fired at 900° C. for ten minutes. The sensor unit incorporating the six sensor elements of sandwich structure is thus realized.

FIG. 20a is a view showing schematically a structure of the sensor unit according to another embodiment of the invention, and FIG. 20b is a sectional view of the same taken along the line XXb—XXb in FIG. 20a. In the case of this embodiment, each of the six sensor elements 2001 to 2006 disposed on a common substrate is of a sheet-like structure, presenting the exposed sensing surface. The process of realizing the sensor unit under consideration is similar to that of the sensor unit shown in FIGS. 19a and 19b. At first, a common refractory insulation substrate 201 is deposited with twelve lower electrodes 202, interconnecting conductors 203 therefor, terminals 2021 to 2026 and 2031 at predetermined locations by employing a gold conductor paste (e.g. paste No. 8760 manufactured by E. I. du Pond de Nemours & Co.). Concurrently, the rear surface of the substrate 201 is deposited with a heater pattern 205 by employing a platinum paste (e.g. aforementioned paste "TR 760A"). The assembly is then subjected to a firing process. Thus, there is prepared the substrate for the sensor unit. Subsequently, gas-sensitive layers 2041 to 2046 are deposited by sputtering same gas-sensitive pastes as those used in the sensor unit shown in FIGS. 19a and 19b.

It will be appreciated that in the case of the sensor units shown in FIGS. 19 and 20 the gas-sensitive pastes themselves are made to differ from one another with a view to realizing mutually different gas detection characteristics. However, it is self-explanatory that the gas detection characteristics can be differentiated from one another even when the same gas-sensitive paste is used, provided that the preparing process and/or manufacturing conditions are varied. The different gas-sensitive characteristics can also be realized even when the sensor elements are partially implemented in an integral structure instead of similar discrete structures.

2-3. Gas Detection Characteristic

Figure 21:
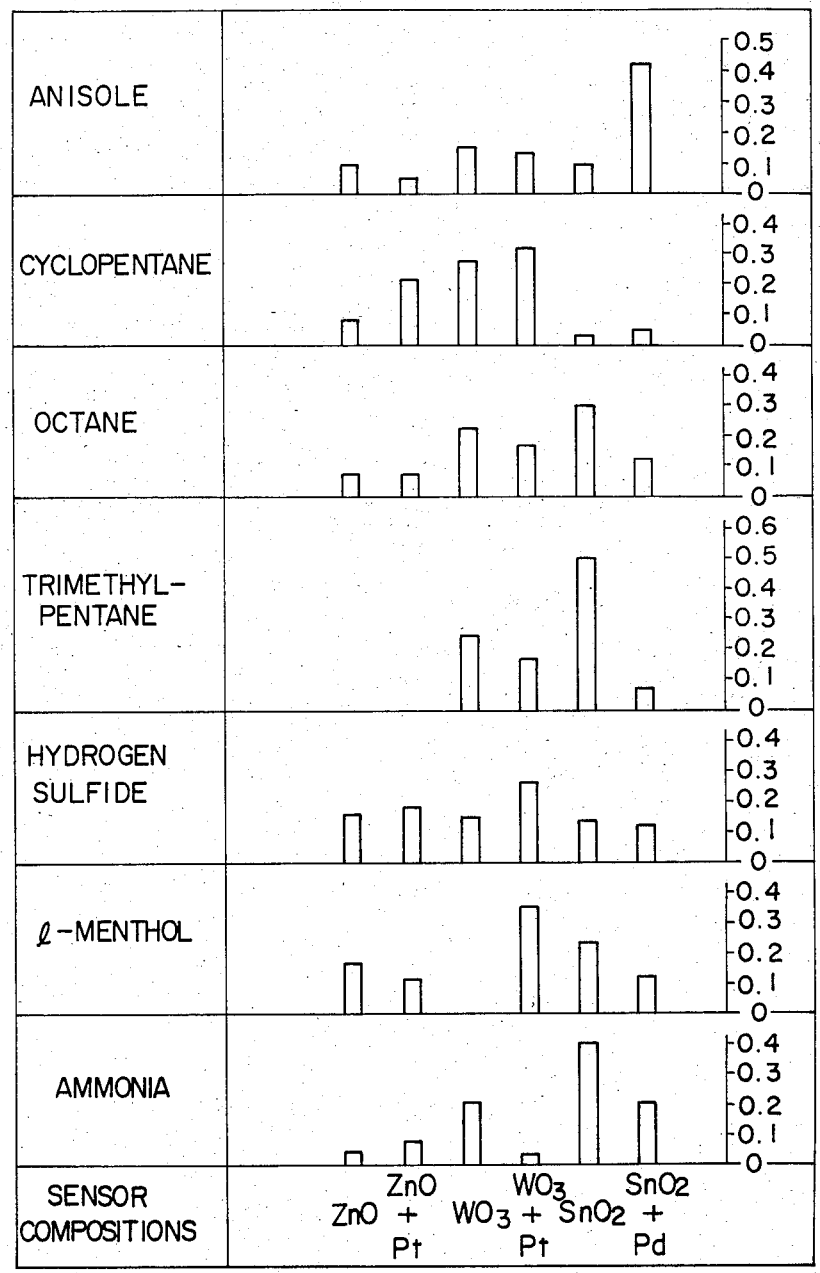
FIG. 21 is a view showing the standard patterns derived from the actually measured data of the gas detection characteristics of the sensor unit shown in FIGS. 19a and 19b.

FIG. 21 shows standard patterns derived from the six sensor elements which are constituted by the aforementioned six different gas-sensitive pastes, respectively, and implemented in the sensor unit of the structure shown in FIGS. 19 for seven sorts of odor and organic solvent vapors, i.e. anisole ($C_7H_8O$), cyclopentane ($C_5H_{10}$), octane ($C_8H_{18}$), trimethylpentane ($C_5H_9(CH_3)_3$), hydrogen sulfide ($H_2S$), l-menthol ($C_{10}H_{20}O$) and ammonia ($NH_3$), respectively. As will be seen from FIG. 21, all of the sensors 1901 to 1902 respond to the presence of all or most of gases except that ZnO- and (ZnO+Pt)-sensors do not respond to trimethylpentane and that $WO_3$-sensor does not respond to l-menthol. Numerical data corresponding to the standard patterns shown in FIG. 21 are listed in table 3.

It should be noted that the conductivity ratios of the sensors whose outputs are to be evaluated for the quantitative determination are previously measured for a number of gas concentrations in view of the fact that the detection outputs of the sensors exhibiting the highest sensitivities to the gases are utilized for the quantitative determination of concentration of the above mentioned odors and organic solvent vapors. The results of measurement are listed in table 4.

TABLE 3

| Gas species | Sensor | | | | | |
|---|---|---|---|---|---|---|
| | ZnO | ZnO + Pt | $WO_3$ | $WO_3$ + Pt | $SnO_2$ | $SnO_2$ + Pd |
| Anisole | 0.097 | 0.060 | 0.157 | 0.157 | 0.097 | 0.432 |
| Cyclopentane | 0.086 | 0.225 | 0.282 | 0.324 | 0.032 | 0.051 |
| Octane | 0.082 | 0.082 | 0.228 | 0.173 | 0.304 | 0.131 |
| Trimethylpentane | 0.000 | 0.000 | 0.251 | 0.170 | 0.501 | 0.078 |
| Hydrogen sulfide | 0.161 | 0.179 | 0.143 | 0.264 | 0.132 | 0.121 |
| l-menthol | 0.176 | 0.118 | 0.000 | 0.353 | 0.235 | 0.118 |
| Ammonia | 0.050 | 0.082 | 0.208 | 0.042 | 0.410 | 0.208 |

TABLE 4

| Gas species | Sensor for quantitative identification | Conductivity ratios (G/Go) depending on gas concentrations | | | | | | | | | |
|---|---|---|---|---|---|---|---|---|---|---|---|
| | | 0.1 | 1.0 | 1.5 | 2.0 | 3.0 | 5.0 | 7.0 | 10.0 | 13.0 | 20.0 |
| Anisole | $SnO_2$ + Pd | 1.21 | 2.54 | 2.88 | 3.16 | 3.60 | 4.26 | 4.75 | 5.34 | 5.82 | 6.71 |
| Cyclopentane | $WO_3$ + Pt | 1.51 | 4.37 | 5.15 | 5.79 | 6.83 | 8.42 | 9.67 | 11.20 | 12.48 | 14.90 |
| Octane | $SnO_2$ | 1.45 | 3.79 | 4.40 | 4.89 | 5.68 | 6.87 | 7.79 | 8.90 | 9.82 | 11.53 |
| Trimethylpentane | $SnO_2$ | 1.20 | 2.44 | 2.76 | 3.01 | 3.42 | 4.01 | 4.46 | 5.00 | 5.43 | 6.23 |
| Hydrogen sulfide | $WO_3$ + Pt | 1.10 | 1.83 | 2.02 | 2.17 | 2.41 | 2.75 | 3.00 | 3.30 | 3.54 | 3.97 |
| l-menthol | $WO_3$ + Pt | 1.14 | 2.09 | 2.33 | 2.52 | 2.83 | 3.27 | 3.61 | 4.00 | 4.31 | 4.89 |
| Ammonia | $SnO_2$ | 1.59 | 4.48 | 5.23 | 5.85 | 6.83 | 8.33 | 9.49 | 10.90 | 12.06 | 14.26 |

2-4. Qualitative And Quantitative Identification Of Detected Gases

Table 5 shows 20 examples of calculation made on trial for qualitative and quantitative identifications of gases on arbitrarily selected conditions. For calculation, the conductivities of the six sensor elements exposed to seven different gases of arbitrarily elected concentrations, respectively were measured, and the detection patterns were arithmetically determined in accordance with the expression (6) mentioned hereinbefore. The gas species whose detection patterns have the minimum or least similarity to the standard patterns were identified, wherein concentrations of the identified gases were estimated on the basis of the numerical data listed in the table 4. Further, estimation of the gas concentrations was effected by resorting to linear interpolation on the basis of the numerical data listed in the table 4.

As will be seen from the table 5, there are coincidence between the actually identified gas species and the results of estimation in all twenty examples of calculation. There is no problem to be mentioned concerning the error in estimation of the gas concentrations.

TABLE 5

| Example of calculation | Conditions | | | Detection pattern | | | | | |
|---|---|---|---|---|---|---|---|---|---|
| | Gas species | Concentration (ppm) | G/Go | ZnO | ZnO + Pt | $WO_3$ | $WO_3$ + Pt | $SnO_2$ | $SnO_2$ + Pd |
| 1 | Hydrogen sulfide | 2.0 | 2.14 | 0.153 | 0.176 | 0.135 | 0.253 | 0.146 | 0.137 |
| 2 | Cyclopentane | 1.0 | 4.32 | 0.071 | 0.225 | 0.262 | 0.318 | 0.048 | 0.076 |
| 3 | Octane | 2.0 | 4.78 | 0.069 | 0.097 | 0.238 | 0.165 | 0.289 | 0.142 |
| 4 | Ammonia | 0.5 | 3.37 | 0.062 | 0.088 | 0.205 | 0.068 | 0.379 | 0.198 |
| 5 | Anisole | 2.0 | 3.02 | 0.087 | 0.064 | 0.148 | 0.176 | 0.114 | 0.411 |
| 6 | Trimethylpentane | 5.0 | 3.91 | 0.009 | 0.021 | 0.238 | 0.158 | 0.476 | 0.098 |
| 7 | l-menthol | 5.0 | 3.31 | 0.165 | 0.135 | 0.021 | 0.333 | 0.218 | 0.128 |
| 8 | Anisole | 8.0 | 4.97 | 0.074 | 0.044 | 0.174 | 0.178 | 0.114 | 0.416 |
| 9 | Octane | 6.0 | 7.23 | 0.102 | 0.074 | 0.214 | 0.162 | 0.312 | 0.136 |
| 10 | l-menthol | 10.0 | 4.08 | 0.159 | 0.132 | 0.018 | 0.341 | 0.246 | 0.104 |
| 11 | Anisole | 20.0 | 6.65 | 0.074 | 0.081 | 0.135 | 0.174 | 0.081 | 0.455 |
| 12 | Ammonia | 2.0 | 5.71 | 0.061 | 0.098 | 0.175 | 0.073 | 0.424 | 0.169 |
| 13 | Cyclopentane | 6.0 | 9.12 | 0.075 | 0.204 | 0.274 | 0.325 | 0.051 | 0.071 |
| 14 | l-menthol | 15.0 | 4.53 | 0.175 | 0.128 | 0.021 | 0.331 | 0.224 | 0.121 |
| 15 | Octane | 15.0 | 10.2 | 0.094 | 0.052 | 0.241 | 0.165 | 0.307 | 0.141 |
| 16 | Hydrogen sulfide | 4.0 | 2.53 | 0.181 | 0.154 | 0.124 | 0.273 | 0.151 | 0.117 |
| 17 | Trimethylpentane | 20.0 | 6.16 | 0.012 | 0.031 | 0.231 | 0.159 | 0.479 | 0.088 |
| 18 | Hydrogen sulfide | 8.0 | 3.13 | 0.184 | 0.165 | 0.131 | 0.257 | 0.128 | 0.135 |
| 19 | Ammonia | 5.0 | 8.13 | 0.031 | 0.091 | 0.197 | 0.077 | 0.389 | 0.215 |
| 20 | Cyclopentane | 15.0 | 13.1 | 0.101 | 0.207 | 0.245 | 0.325 | 0.051 | 0.071 |

| Example of calculation | Similarity (minimum value in ◯) | | | | | | | Estimation | |
|---|---|---|---|---|---|---|---|---|---|
| | $S^1$ | $S^2$ | $S^3$ | $S^4$ | $S^5$ | $S^6$ | $S^7$ | Concentration (ppm) | Error (%) |
| 1 | 0.116 | 0.054 | 0.054 | 0.204 | (0.001) | 0.040 | 0.144 | 1.9 | −5 |
| 2 | 0.194 | (0.002) | 0.111 | 0.283 | 0.036 | 0.129 | 0.248 | 0.98 | −2 |
| 3 | 0.130 | 0.118 | (0.001) | 0.063 | 0.059 | 0.107 | 0.036 | 1.89 | −6 |
| 4 | 0.147 | 0.233 | 0.022 | 0.053 | 0.127 | 0.164 | (0.002) | 0.65 | 30 |
| 5 | (0.001) | 0.202 | 0.121 | 0.283 | 0.111 | 0.165 | 0.152 | 1.75 | −13 |
| 6 | 0.271 | 0.276 | 0.040 | (0.002) | 0.187 | 0.190 | 0.036 | 4.66 | −7 |
| 7 | 0.167 | 0.123 | 0.086 | 0.208 | 0.029 | (0.002) | 0.179 | 5.24 | 5 |
| 8 | (0.002) | 0.206 | 0.122 | 0.277 | 0.121 | 0.180 | 0.153 | 8.12 | 2 |
| 9 | 0.137 | 0.140 | (0.001) | 0.056 | 0.063 | 0.096 | 0.032 | 5.78 | −4 |
| 10 | 0.192 | 0.133 | 0.085 | 0.192 | 0.037 | (0.001) | 0.178 | 10.8 | 8 |
| 11 | (0.003) | 0.231 | 0.163 | 0.344 | 0.139 | 0.199 | 0.193 | 19.5 | −3 |
| 12 | 0.186 | 0.259 | 0.029 | 0.043 | 0.142 | 0.161 | 0.004 | 1.89 | −6 |
| 13 | 0.196 | (0.001) | 0.108 | 0.274 | 0.038 | 0.130 | 0.248 | 6.12 | 2 |
| 14 | 0.172 | 0.127 | 0.085 | 0.204 | 0.031 | (0.001) | 0.178 | 15.7 | 5 |
| 15 | 0.136 | 0.141 | (0.001) | 0.053 | 0.071 | 0.110 | 0.034 | 14.6 | −3 |
| 16 | 0.133 | 0.060 | 0.059 | 0.207 | (0.002) | 0.030 | 0.158 | 3.71 | −7 |
| 17 | 0.278 | 0.274 | 0.040 | (0.002) | 0.184 | 0.186 | 0.037 | 19.4 | −3 |
| 18 | 0.118 | 0.057 | 0.065 | 0.225 | (0.001) | 0.040 | 0.162 | 8.3 | 4 |
| 19 | 0.146 | 0.244 | 0.027 | 0.052 | 0.137 | 0.170 | (0.002) | 4.73 | −5 |
| 20 | 0.190 | (0.003) | 0.107 | 0.280 | 0.028 | 0.110 | 0.247 | 14.8 | −1 |

It will be appreciated that a great number of gases can be identified qualitatively and quantitatively independent of the number of the incorporated sensor elements, so long as the standard patterns for the gases to be detected are different from one another.

2.5. System Structure

In this section, description is made on a structure of the odor/organic solvent vapor detecting apparatus incorporating the aforementioned sensor elements and an arithmetic processing method.

2-5-1. Processing Circuit

Figure 22:
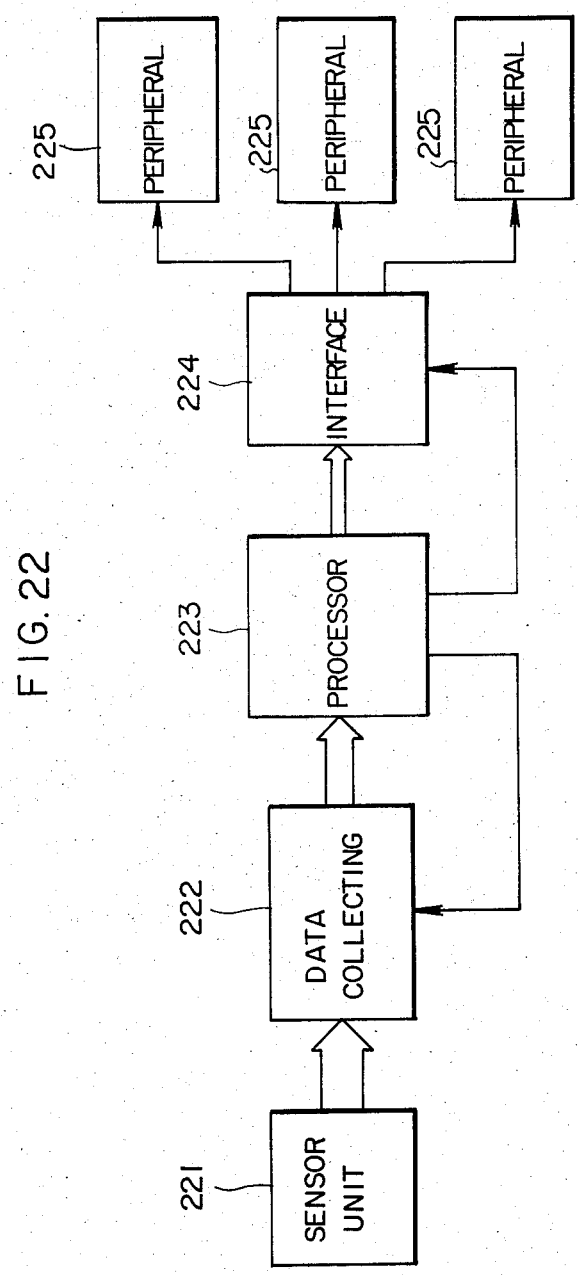
FIG. 22 is a schematic diagram of an arithmetic processing circuit for the gas detecting apparatus according to a second exemplary embodiment of the invention.

FIG. 22 shows schematically in a block diagram a general arrangement of the odor/organic solvent vapor detecting apparatus. The sensor unit 221 incorporates the six sensor elements constituted by the aforementioned materials or compositions. The detection outputs of the sensor elements are amplified by a data collecting device 222 under control of a processor 223 and converted into digital signals which are fetched by the processor 223. Arithmetic processing executed internally of the processor 223 will hereinafter be described in greater detail. A predetermined number of peripheral devices 225 are connected to the processor 223 through an interface 224. When the processor makes a decision on the basis of the results of the arithmetic processing that transmission of information or control operation should be performed, one or more peripheral devices 225 are correspondingly operated for the transmission of information or for the environmental amelioration. Such peripheral device may include signal devices capable of producing information or signals perceivable by human being such as, for example, monitor television system, digital display, alarm lamp, and alarm buzzer, ventilation or air conditioning system and apparatus which generate odor and/or organic solvent vapor.

2-5-2. Flow Chart Of Arithmetic Processing

Figure 18B:
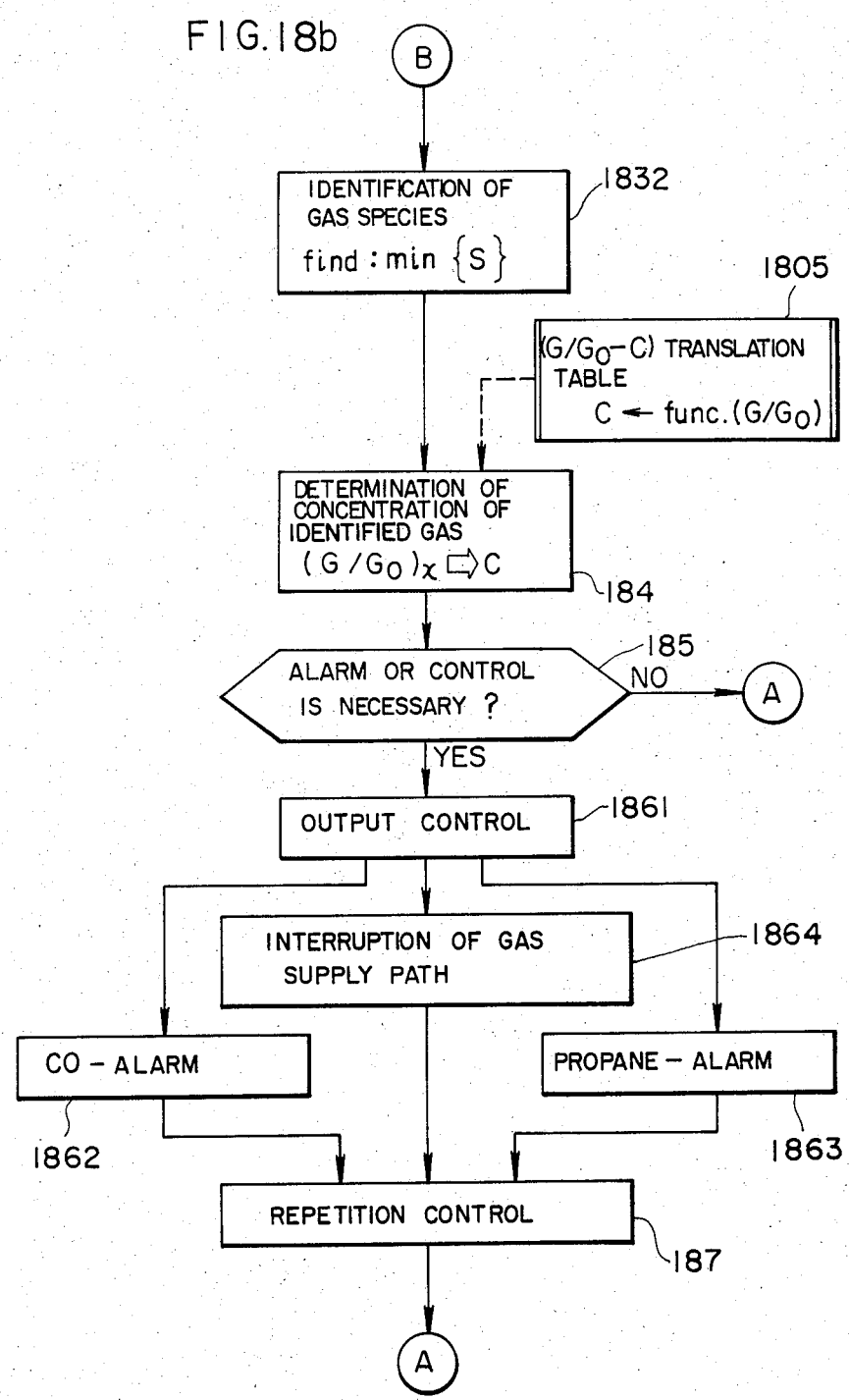

Also in the case of the instant example 2, the arithmetic processing can be executed in principle through substantially same steps as those described hereinbefore in conjunction with the example 1 by referring to FIG. 18. Description will be made briefly on program for the arithmetic processing executed by the processor 223 by referring to FIG. 23. When the start is commanded at a step 231, the data collecting device 222 is put into operation to effect collection of data signals and A/D conversion thereof at a step 2321, whereby 10-bit digital values $\vec{V}$ are derived from the average values resulted from A/D conversion of the analog detection voltages $\vec{V}$ produced by the sensor unit 221. On the basis of these digital values $\vec{V}$ and numerical values cited from a V-$G/G_0$ translation table 2301 stored previously in the processor, voltage-to-conductivity ratio translation is effected at a step 2322. The conductivity ratios ($G/G_0$) thus obtained are then subjected to a conductivity ratio-to-logarithm translation at a step 2323, to derive $\vec{y} = -\{\log(G/G_0)\}$. Argument of the translation table is prepared on the basis of most significant six bits of the digital values $\vec{V}$, ($G/G_0$) in accordance with the expression (17). Further, by making use of the remaining four bits, linear interpolation is performed in accordance with the expression (19) as in the case of the preceding example 1. Next, at a step 233, arithmetic determination of the detection patterns $\vec{x}$ is executed in accordance with the following expression (23):

$$\vec{x} = \frac{1}{\sum_j y_j} \vec{y} \qquad (23)$$

On the basis of the detection patterns thus determined and the standard patterns $\vec{p_i}$ and weights $\vec{w_i}$ read out from the stored standard pattern $(\vec{p})$ table 2303 and weight $(\vec{W})$ table 2304, respectively, calculation of similarities $S_i$ is performed at a step 234 in accordance with $$S_i = \{\|\vec{W_i}(\vec{x}-\vec{p_i})\|_2\}^2 \qquad (24)$$

Among these similarities $S_i$, the minimum one is determined to identify the gas species at a step 235. In dependence on the results of the gas species identification, the sensor element whose output is to be evaluated for quantitative determination of the gas concentration is selected. On the basis of conductivity ratio of the selected sensor element and data cited from the stored $G/G_0$-to-C translation table 2305, the step 236 for quantitative determination of concentration of the detected gas is executed. Finally, from the results of the gas species identification and the quantitative determination of gas concentration, a decision step 237 is executed as to whether alarm or control be commanded or not. If the decision step results in "NO", the processing is again performed starting from the step 2321. On the other hand, when the decision step results in "YES", interface control step 2381 is performed to trigger operation of the peripheral device at a step 2382. The alarm or control operation is sustained through a repetition control step 239. The processing is again initiated from the step 2321.

By virtue of the structure of the apparatus and the arithmetic processing method described above, any given odor and organic solvent vapor can be qualitatively and quantitatively identified with increased reliability at high precision and speed on a real-time basis. Further, a great number of gas species which exceeds the number of the incorporated gas sensor elements can be identified qualitatively and quantitatively.

EXAMPLE 3

Figure 24:
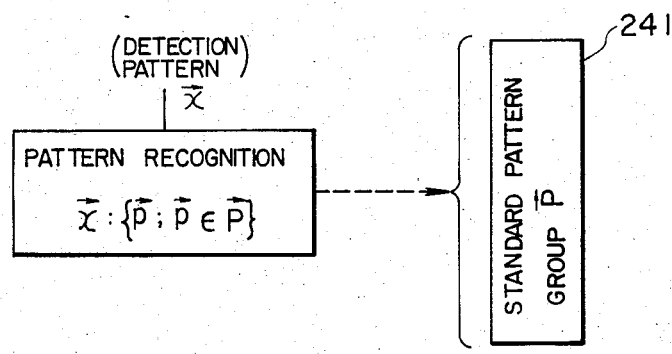
FIG. 24 shows a flow chart for illustrating pattern recognition processing which may be adopted in the arithmetic processing procedures executed by the first and second embodiments of the invention.

The pattern recognition procedure described in conjunction with the examples 1 and 2 is based on the comparison in accordance with the expression (24) between the detection patterns $\vec{x}$ and a element $\vec{p}$ of the group $\vec{P}$ of the standard patterns (241) of the structure similar to that of the detection patterns (in respect to the equal number of elements of patterns and identical numerical conditions), as is shown in FIG. 24. In particular, the number of the elements is equal to the number of the incorporated sensor elements. However, in conjunction with the examples 1 and 2, it is obvious without resorting to illustration that procedures mentioned below may be adopted in the course of the pattern recognition processing executed for the patterns.

Figure 25:
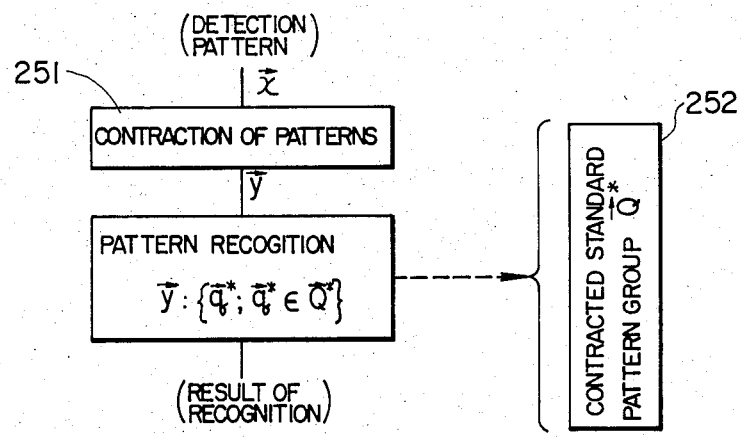
FIGS. 25 and 26 are flow charts for illustrating another pattern recognition processing according to a third exemplary embodiment of the invention.

(1) Instead of limiting the number of elements of patterns to be handled to the number of the incorporated sensor elements, numerical values arithmetically determined secondarily from some of the detection outputs (e.g. the outputs of the sensor elements which respond simultaneously to the presence of a certain gas and which allow, when arithmetically processed through addition, multiplication or the like, the presence of the certain gas to be made more distinctive) may be added as the elements of pattern and at the same time those elements which are less effective for pattern recognition are deleted to contract correspondingly the pattern, for thereby enhancing the speed and accuracy of the pattern recognition processing operation. In this case, the processing is performed in the manner shown in FIG. 25. More particularly, the detection pattern $\vec{x}$ is contracted (251) in accordance with the expression (25)

mentioned below to be translated to the contracted pattern $\vec{y}$, wherein the pattern recognition processing is carried out by comparing the contracted standard patterns $\vec{q}*$ (having the structure similar to that of the aforementioned contracted pattern y) which are members of a group of the contracted standard patterns $\vec{Q}*$ (252).

If $\vec{x} = \{\vec{x_1}, \vec{x_2}, \vec{x_3}\}$, .

$$\vec{y} = \{\vec{x_1}, \text{func.}(\vec{x_1}, \vec{x_2})\} \quad (25)$$

where $\vec{x_1}$ is reserved as it is, $\vec{x_2}$ and $\vec{x_3}$ are deleted with the elements processed from $\vec{x_1}$ and $\vec{x_2}$ being added.

Figure 26:
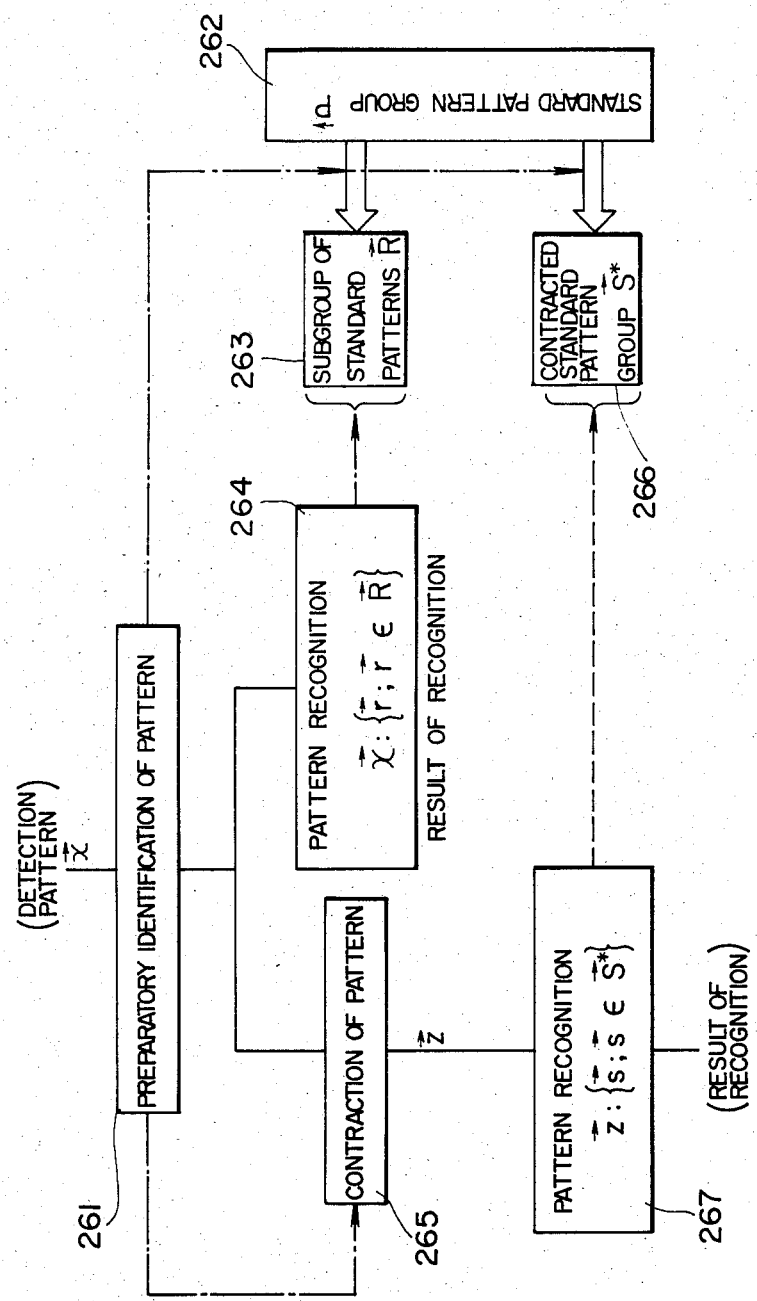

(2) Assuming now that the standard pattern group $\vec{P}$ is previously classified into subgroups in accordance with some characteristic quantities (e.g. magnitude of the numerical values, relative difference between the elements or the like), the corresponding part of the detection pattern $\vec{x}$ is examined to determine the presence or absence of the similar characteristic quantities, i.e. the detection pattern $\vec{x}$ is preparatorily identified (261), as is illustrated in FIG. 26, whereby the standard patterns to be subjected to the pattern recognition processing are restricted to the standard patterns $\gamma$ belonging to the standard pattern subgroup $\vec{R}(\epsilon\vec{P}, 263)$ having the corresponding characteristics instead of processing all the patterns belonging to the standard pattern group $\vec{P}$ (262), to thereby realize the speed-up of the pattern recognition processing (264).

Further the pattern contracting method (265) may be varied in dependence on the preparatory identification (261) of the detection pattern to arithmetically determine the contracted pattern which is most effective for the pattern recognition processing involved in the identification in concern, whereby the pattern recognition processing is restricted to the contracted standard patterns s* (having similar structure to the contracted pattern Z) which are the elements of the contracted standard pattern group S* (266) corresponding to the patterns Z. In this way, speed-up of the pattern recognition processing (267) can be attained.

(3) In case the standard pattern group mentioned above in conjuction with (1) and (2) is arrayed regularly in the order of magnitude of values of certain elements or relative ratio between particular elements, acquisition of the most similar pattern can be accomplished with increased efficiency by adopting a well known search procedure (e.g. binary search or dichotomizing search).

By adopting the procedure described above, the arithmetic processing for the pattern recognition involved in identification of given odor or organic solvent vapor can be executed at an increased speed with high accuracy.

EXAMPLE 4

Relative to the examples 1 to 3, description has been made on the presumption that the standard patterns are previously stored in the memory such as ROM. In contrast, description of the instant example is directed to such an arrangement of the apparatus in which addition, deletion and correction of given standard patterns in addition to the previously stored standard patterns are permitted externally of the apparatus. As an example of application of such apparatus, suppose that the sensors are installed at kitchen or other locations for detecting odors, and that one of the peripheral devices shown in FIG. 22 is constituted by a ventilator fan for expelling the odor. In that case, unless the odor originates in a toxic gas, the ventilating fan may be activated only when the odor has attained the level at which man feels abhorrence to the odor. In the instant example, it is contemplated to preset that level of the odor in a memory through manual operation. The instant example will be described in conjunction with the odor/organic solvent vapor detecting apparatus provided with the sensor unit and the arithmetic processing procedure mentioned in the preceeding example 2.

4-1. Processing Circuit

Figure 27:
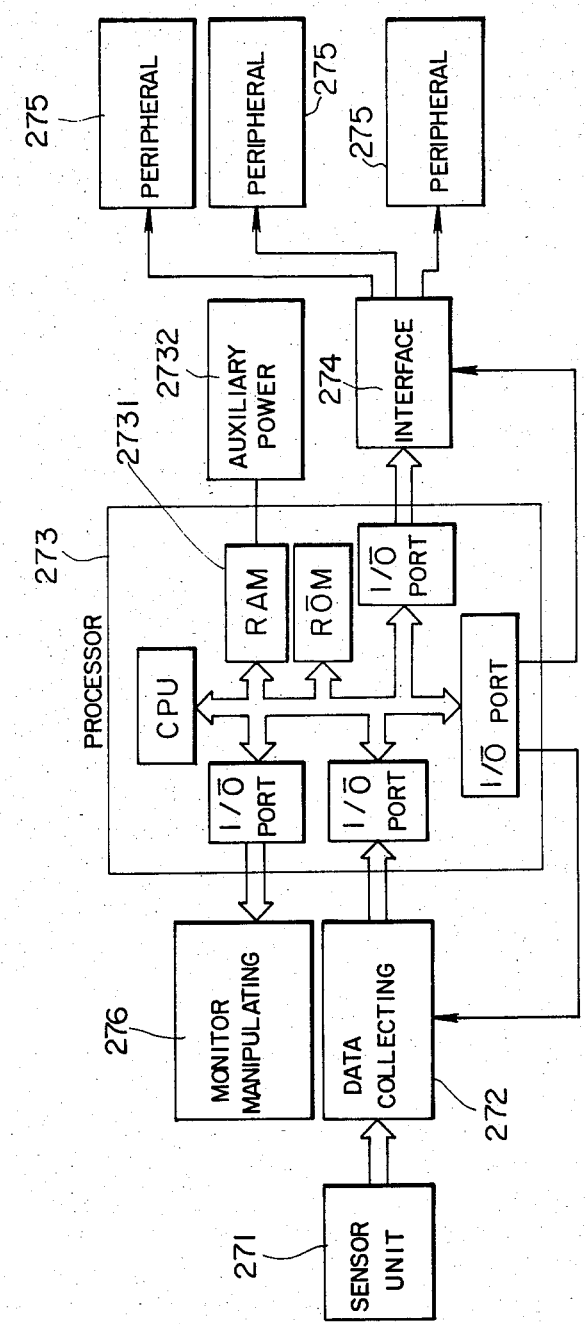
FIG. 27 is a schemative diagram showing an arithmetic processing circuit for the gas detecting apparatus according to a fourth exemplary embodiment of the invention.

FIG. 27 shows schematically an arrangement of the apparatus according to the instant example. The fundamental parts of the apparatus are same as those shown in FIG. 22. Accordingly, description is centered on those features which differentiate the apparatus under consideration from that shown in FIG. 22. More particularly, both apparatus are similar in that the signals from the sensor unit 271 are fetched by the processor 273 through the data collecting circuit 272, wherein the operation of the peripheral device 275 is controlled in dependence on the result of the arithmetic processing performed by the processor 273 by way of the interface 274. In the case of the instant example, however, a monitor on manipulating device 276 is so provided as to be capable of performing data transfer with the processor 273. With the aid of this manipulating device 276, interrupt may be made to the arithmetic processing executed by the processor 273 for effecting addition, deletion or correction of information concerning the standard patterns stored in the RAM 2731. The latter is provided with an auxiliary power source 2732 to preserve the stored contents even in the outage.

4-2. Flow Chart Of Arithmetic Processing

Figure 23A:
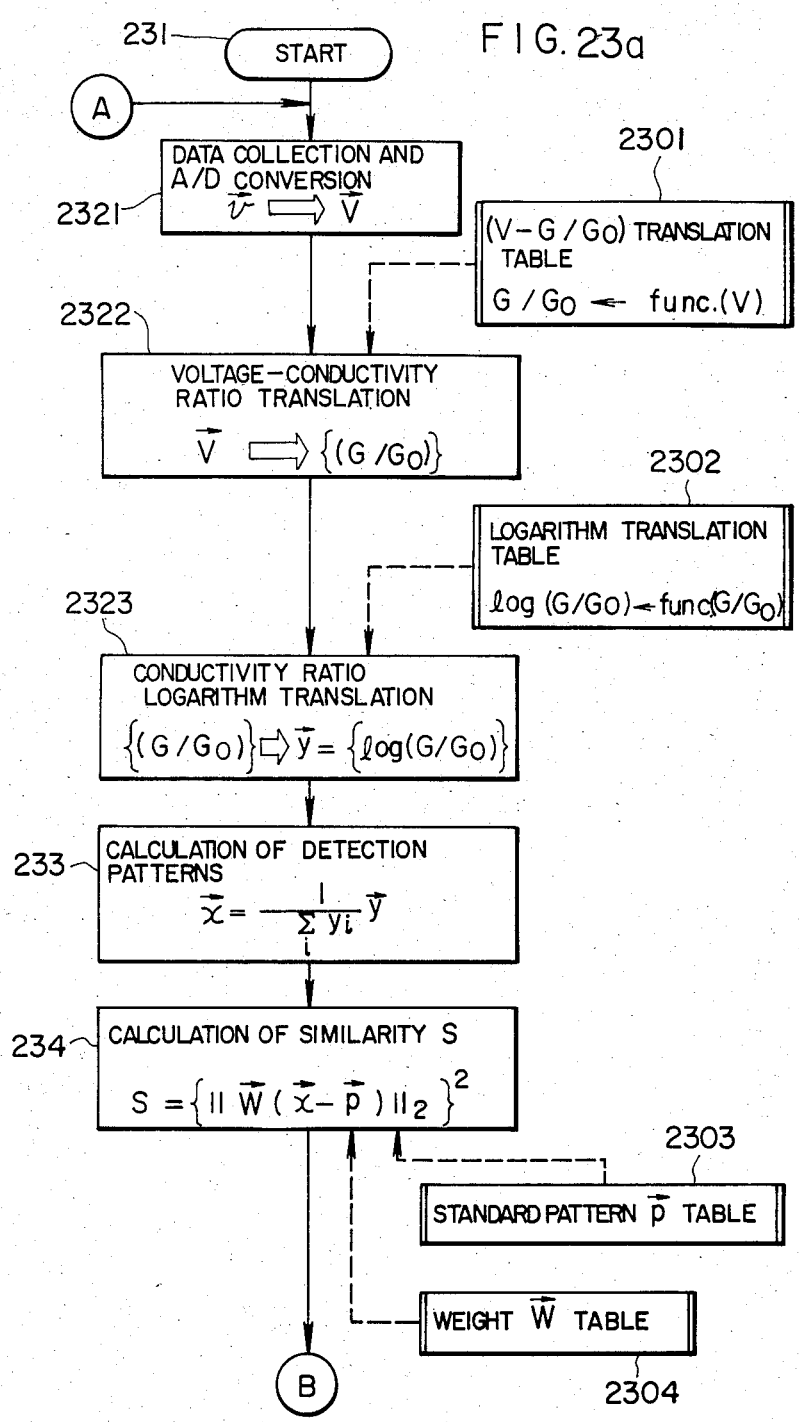
FIGs. 23a and 23b show a flow chart for illustrating arithmetic processing procedures executed in the gas detecting apparatus according to the second embodiment of the invention.
Figure 23B:
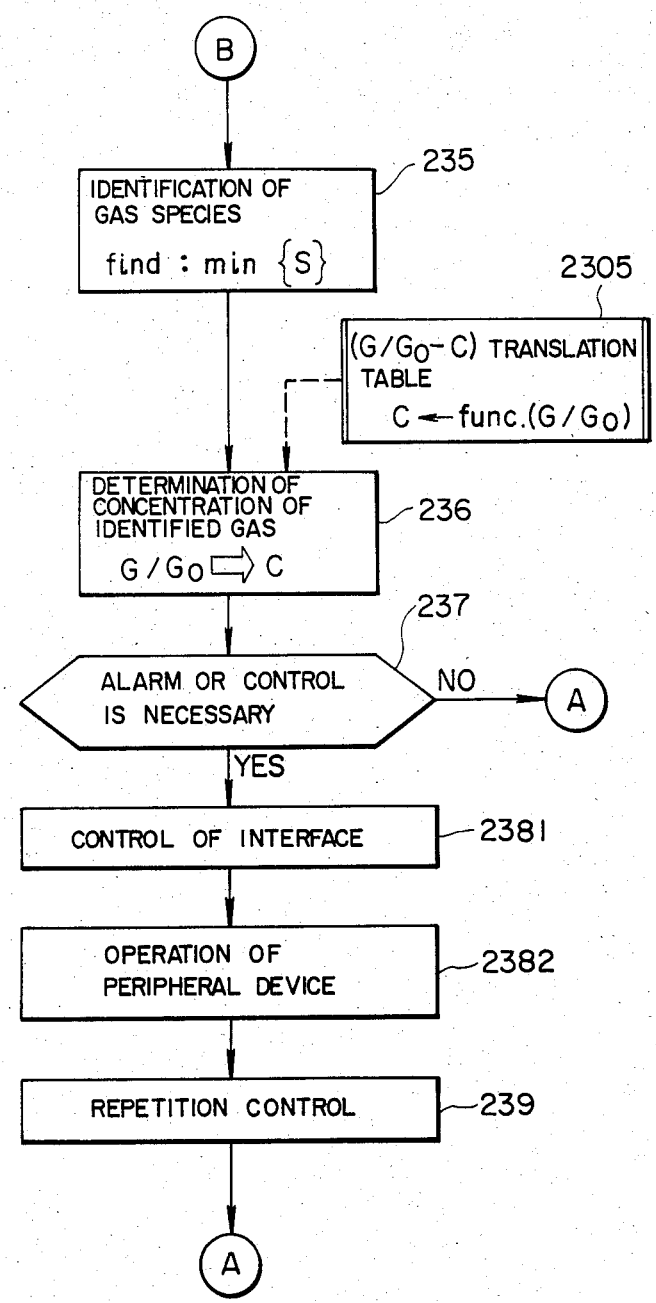
Figure 28:
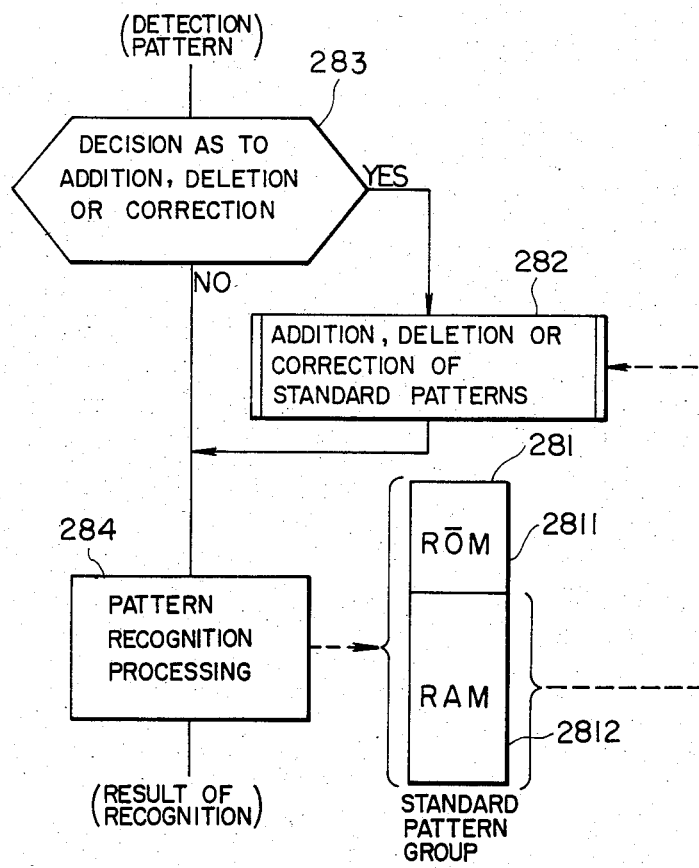
FIG. 28 is a flow chart for illustrating arithmetic processing procedure executed by the fourth embodiment of the invention.

Since the fundamental feature of the arithmetic processing program is same as that of the program shown in FIG. 23, description will be made only of the different points by referring to FIG. 28.

The standard pattern group 281 are stored in both of RAM 2812 and ROM 2811. Although the contents of ROM 2811 can not be modified, it is easy to modify the contents of the RAM 2812. Assuming now that interrupt is issued externally of the apparatus for performing addition, deletion and correction of the standard patterns, and interrupt processing subroutine 282 is activated for allowing the addition, deletion and correction of the standard patterns while transferring information with the external device. Discrimination of the interrupt is effected at the step 283. With this interrupt, it is possible to store additionally a detection pattern arithmetically determined on certain conditions in the RAM 2812 as the standard pattern or alternatively delete or correct the standard pattern in dependence on the detection pattern.

It is apparent that at the pattern recognition processing step 284, the concept mentioned in conjunction with the example 3 can be adopted.

By virtue of the structure of the apparatus and arithmetic processing described above, a so-called learning function for permitting appropriate addition, deletion and alteration of the sorts of odor and/or organic solvent vapor can be realized, to a great advantage. This apparatus makes a great contribution to the manufacturing of the apparatus on a mass production basis, increasing of the reliability, and expansion of the applicability owing to capability of expanding the function and utility of the apparatus by users.

Effect of the Invention

With the gas detecting apparatus according to the invention, a great variety of gases, odors or organic solvent vapors can be qualitatively and quantitatively identified.

No specific requirements such as, for example, response to only the specified sorts of gases are imposed on the incorporated gas sensor elements. Since the sensor unit can serve practical purposes so far as some relative differences exist among the gas detection characteristics of the individual gas sensor elements, inexpensive materials can be used for implementing the sensor elements while the apparatus can be used for practical applications without need for development of the sensor elements which satisfy specific requirements.

Further, since the characteristic values referred to in the course of arithmetic processing as well as preset signals can be altered from the outside of the apparatus, increased number of various gases, odors, organic solvent vapors and the like can be qualitatively and quantitatively identified with the single apparatus of predetermined specification. It will now be appreciated that the present invention has provided an inexpensive gas detecting apparatus which can enjoy numerous applications over extended range, to great advantages to the art.

We claim:

1. A gas detecting apparatus comprising:
   a plurality of gas detecting semiconductor elements having gas detection characteristics differing from one another;
   storage means for storing a plurality of standard patterns prepared by measuring previously the gas detection characteristics of said gas detecting semiconductor elements in dependence on species of gas components and mixing ratios thereof and patterning the measured detection characteristics; and
   arithmetic means for arithmetically processing gas detection outputs of said plural gas detecting semiconductor elements, said arithmetic means including means for comparing a detected pattern reproduced from gas detection outputs of said plural gas detecting semiconductor elements with said standard patterns stored in said storage means for identifying the species of a gas to be detected.

2. A gas detecting apparatus according to claim 1, further comprising means for providing said standard patterns in a form of a vector represented in a histogram obtained by quantizing analog outputs from said gas detecting semiconductor elements having said gas detection characteristics.

3. A gas detecting apparatus according to claim 1, further comprising means for obtaining said standard patterns by taking logarithms of outputs from said gas detecting semiconductor elements having said gas detection characteristics and by dividing each of said logarithms by the total thereof so as to standardize these logarithms so that said standard patterns have a common shape independent from a concentration of each mixed gas.

4. A gas detecting apparatus according to claim 1, further comprising means for providing said standard patterns only for a specified gas to improve a capability of identifying the specified gas.

5. A gas detecting apparatus according to claim 1, further comprising means for determining said standard patterns to have a specific characteristic different from one another among species of gas components, respectively so as to enable to identify said gas components.

6. A gas detecting apparatus according to claim 1, wherein said storage means includes a random access memory in which detection patterns derived through arithmetic processing effected by said arithmetic means are stored as the standard patterns.

7. A gas detecting apparatus comprising:
   a plurality of gas detecting semiconductor elements having gas detection characteristics differing from one another;
   storage means for storing a plurality of standard patterns prepared by measuring previously the gas detection characteristics of said gas detecting semiconductor elements in dependence on species of gas components and mixing ratios thereof and patterning the measured detection characteristics; and
   arithmetic means for arithmetically processing gas detection outputs of said plural gas detecting semiconductor elements, said arithmetic means including means for comparing a detected pattern reproduced from the gas detection outputs of said plural gas detecting semiconductor elements with the standard patterns stored in said storage means for identifying the species of a gas to be detected, while a quanititative determination of concentration of the gas to be detected is made on the basis of the detection output from the particular one of said semiconductor elements which exhibits the highest sensitivity to said gas to be detected.

* * * * *